(12) United States Patent
Sauer

(10) Patent No.: US 10,736,624 B2
(45) Date of Patent: Aug. 11, 2020

(54) MINIMALLY INVASIVE SURGICAL SUTURING DEVICE FOR PAPILLARY MUSCLES AND METHODS THEREOF

(71) Applicant: LSI Solutions, Inc., Victor, NY (US)

(72) Inventor: Jude S. Sauer, Pittsford, NY (US)

(73) Assignee: LSI Solutions, Inc, Victor, NY (US)

( * ) Notice: Subject to any disclaimer, the term of this patent is extended or adjusted under 35 U.S.C. 154(b) by 537 days.

(21) Appl. No.: 14/716,803

(22) Filed: May 19, 2015

(65) Prior Publication Data

US 2015/0359531 A1 Dec. 17, 2015

Related U.S. Application Data

(60) Provisional application No. 62/000,280, filed on May 19, 2014.

(51) Int. Cl.
*A61B 17/04* (2006.01)
*A61F 2/24* (2006.01)
(Continued)

(52) U.S. Cl.
CPC ...... *A61B 17/0482* (2013.01); *A61B 17/0401* (2013.01); *A61B 17/0469* (2013.01);
(Continued)

(58) Field of Classification Search
CPC ... A61F 5/08; A61B 17/0482; A61B 17/0401; A61B 2017/0406; A61B 2017/0404
See application file for complete search history.

(56) References Cited

U.S. PATENT DOCUMENTS

| | | | |
|---|---|---|---|
| 5,431,666 | A | 7/1995 | Sauer |
| 5,562,686 | A | 10/1996 | Sauer |

(Continued)

FOREIGN PATENT DOCUMENTS

| | | |
|---|---|---|
| EP | WO1998053745 | 12/1998 |
| EP | WO2016118869 | 7/2016 |

OTHER PUBLICATIONS

Sep. 16, 2016 International Search Report; PCT—Written Opinion of the International Searching Authority in corresponding International Application No. PCT/US2016/033234.
(Continued)

*Primary Examiner* — Shaun L David
*Assistant Examiner* — Christina C Lauer
(74) *Attorney, Agent, or Firm* — David J. Gervasi; Christopher B. Miller

(57) ABSTRACT

A surgical suturing device is disclosed. The surgical suturing device has a forked guide tip having a plurality of legs, wherein each of the plurality of legs comprises a proximal end, an anatomical variation, and a distal end. A method of chord replacement for a heart valve is also disclosed. A suture is placed in a papillary muscle using a surgical suturing device having a forked guide tip and a papillary suture. A leaflet suture is placed in a leaflet. The papillary suture and the leaflet suture are loaded in a suture fastener from opposite directions in a coaxial fashion. The length of the papillary suture and/or the leaflet suture are adjusted relative to the suture fastener to achieve a desired replacement chord length. The suture fastener is attached to the papillary suture and the leaflet suture to lock the desired replacement chord length.

16 Claims, 20 Drawing Sheets

(51) Int. Cl.
  *A61B 17/062* (2006.01)
  *A61B 17/00* (2006.01)
(52) U.S. Cl.
  CPC ........ *A61B 17/0625* (2013.01); *A61F 2/2457* (2013.01); *A61F 2/2466* (2013.01); *A61B 17/0487* (2013.01); *A61B 2017/00243* (2013.01); *A61B 2017/0406* (2013.01); *A61B 2017/0409* (2013.01); *A61B 2017/0472* (2013.01)

(56) References Cited

U.S. PATENT DOCUMENTS

| | | |
|---|---|---|
| 6,997,931 B2 | 2/2006 | Sauer |
| 7,407,505 B2 | 8/2008 | Sauer |
| 7,731,727 B2 | 6/2010 | Sauer |
| 8,313,496 B2 | 11/2012 | Sauer |
| 8,398,657 B2 | 3/2013 | Sauer |
| 2003/0236535 A1* | 12/2003 | Onuki ................ A61B 17/0482 606/144 |
| 2004/0133238 A1 | 7/2004 | Cerier |
| 2005/0119735 A1 | 6/2005 | Spence |
| 2005/0251153 A1* | 11/2005 | Sakamoto .......... A61B 17/0469 606/139 |
| 2007/0100348 A1* | 5/2007 | Cauthen, III ........ A61B 17/068 606/99 |
| 2008/0065120 A1 | 9/2008 | Zannis |
| 2009/0222027 A1 | 9/2009 | Sauer |
| 2011/0306989 A1 | 12/2011 | Darois et al. |
| 2012/0016383 A1* | 1/2012 | Sauer et al. ........ A61B 17/0482 606/148 |
| 2015/0282805 A1* | 10/2015 | Sauer ................. A61B 17/0482 606/145 |

OTHER PUBLICATIONS

Jan. 21, 2019 Extended European Search Report; Mathis, Martin, Extended European Search Report for EP16797289.

* cited by examiner

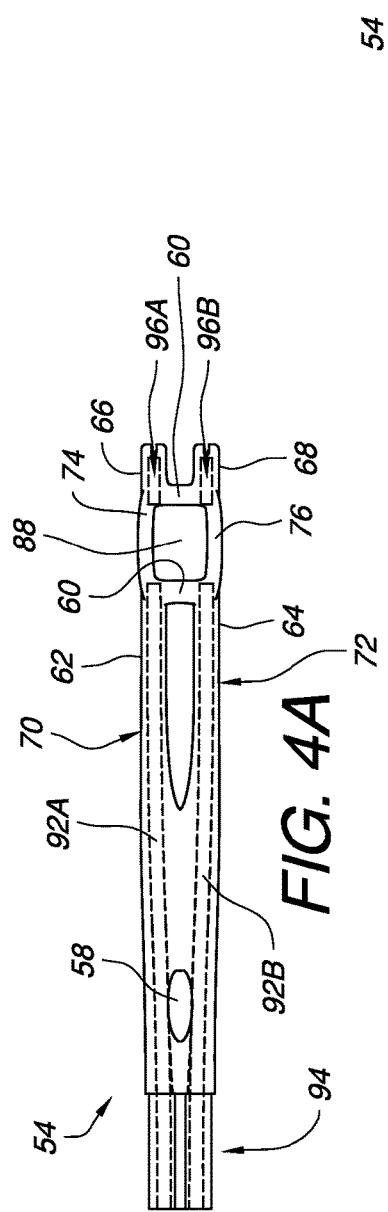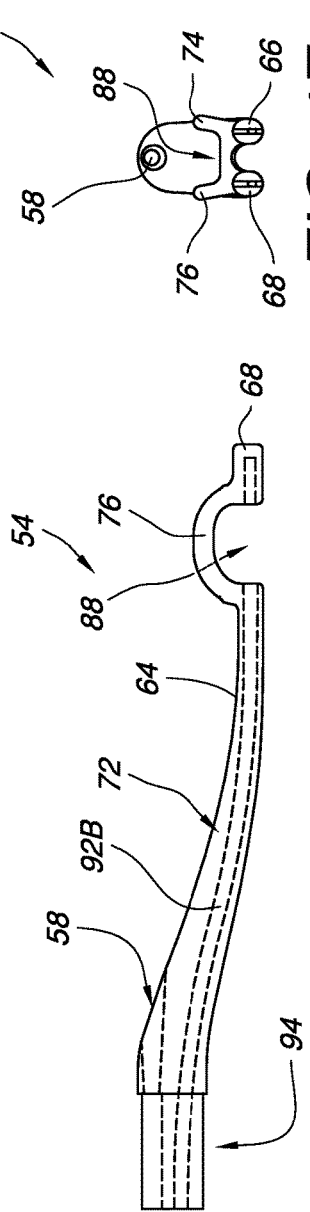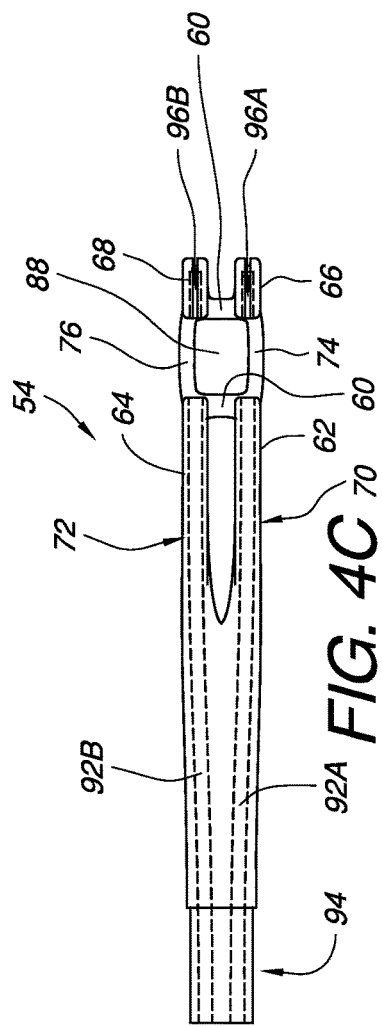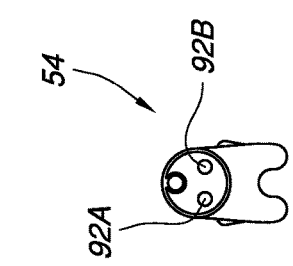

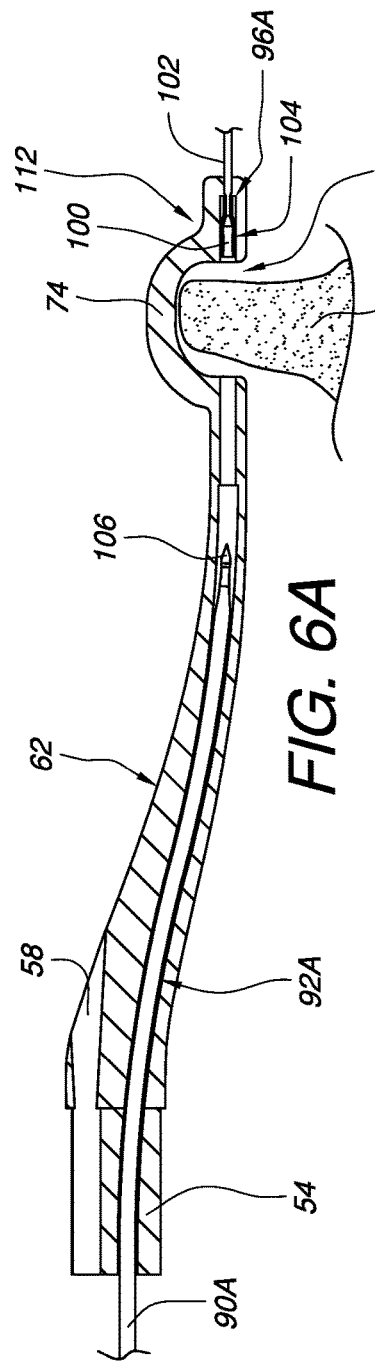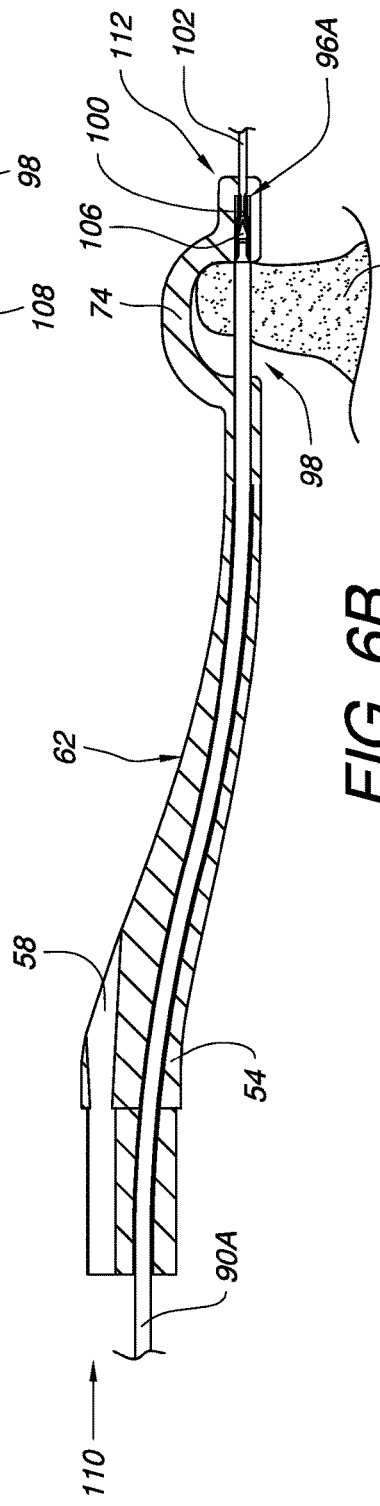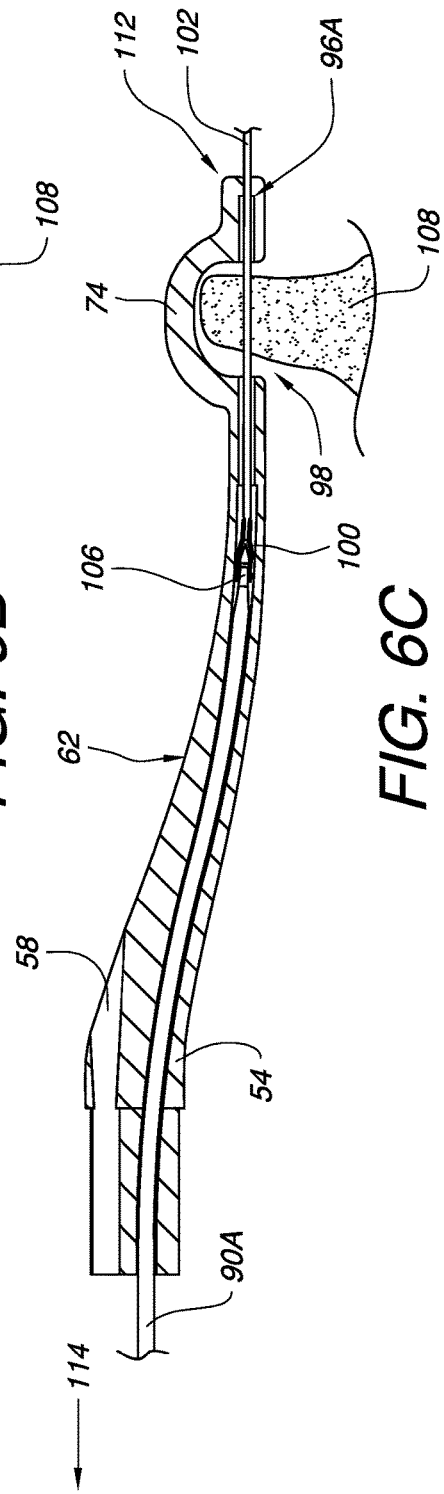

MINIMALLY INVASIVE SURGICAL SUTURING DEVICE FOR PAPILLARY MUSCLES AND METHODS THEREOF

RELATED APPLICATION

This patent application claims priority to U.S. Provisional Patent Application 62/000,280 filed May 19, 2014 and entitled, "MINIMALLY INVASIVE SURGICAL SUTURING DEVICE FOR PAPILLARY MUSCLES AND METHODS THEREOF". The entire provisional patent application 62/000,280 is hereby incorporated by reference in its entirety.

FIELD

The claimed invention relates to surgical suturing, and more specifically to minimally invasive surgical suturing devices and methods for suturing papillary muscles.

BACKGROUND

The human heart relies on a series of one-way valves to help control the flow of blood through the chambers of the heart. For example, referring to FIG. 1, deoxygenated blood returns to the heart 20, via the superior vena cava 22 and the inferior vena cava 24, entering the right atrium 26. The heart muscle tissue contracts in a rhythmic, coordinated heartbeat, first with an atrial contraction which aids blood in the right atrium 26 to pass through the tricuspid valve 28 and into the right ventricle 30. Following atrial contraction, ventricular contraction occurs and the tricuspid valve 28 closes. Ventricular contraction is stronger than atrial contraction, assisting blood flow through the pulmonic valve 32, out of the heart 20 via the pulmonary artery 34, and to the lungs (not shown) for oxygenation. Following the ventricular contraction, the pulmonic valve 32 closes, preventing the backwards flow of blood from the pulmonary artery 34 into the heart 20.

Oxygenated blood returns to the heart 20, via the pulmonary veins 36, entering the left atrium 38. Left atrial contraction assists blood in the left atrium 38 to pass through the mitral valve 40 and into the left ventricle 42. Following the atrial contraction, ensuing ventricular contraction causes mitral valve 40 closure, and pushes oxygenated blood from the left ventricle 42 through the aortic valve 44 and into the aorta 46 where it then circulates throughout the body. Under nominal conditions, prolapse of mitral valve 40 is prevented during ventricular contraction by chordae 40A attached between the mitral valve 40 leaflets and papillary muscles 40B. Following left ventricular contraction, the aortic valve 44 closes, preventing the backwards flow of blood from the aorta 46 into the heart 20.

Unfortunately, one or more of a person's heart valves 28, 32, 40, and 44 can have or develop problems which adversely affect their function and, consequently, negatively impact the person's health. Generally, problems with heart valves can be organized into two categories: regurgitation and/or stenosis. Regurgitation occurs if a heart valve does not seal tightly, thereby allowing blood to flow back into a chamber rather than advancing through and out of the heart. This can cause the heart to work harder to remain an effective pump. Regurgitation is frequently observed when the mitral valve 40 fails to properly close during a ventricular contraction. Mitral regurgitation can be caused by chordae 40A stretching, tearing, or rupture, along with other structural changes within the heart.

Neochordal replacement for stretched or torn chordae is one option to reduce regurgitation. In such a procedure, chords to be replaced are identified and dissected as required. A papillary suture is placed in a papillary muscle corresponding to the dissected chord. The papillary suture may optionally be pledgeted on one or both sides of the papillary muscle. A leaflet suture is also placed in the corresponding mitral valve leaflet. The papillary suture and the leaflet suture may then be tied or otherwise fastened together to create a replacement chord to help support the mitral valve leaflet and prevent regurgitation.

Unfortunately, while neochordal replacement with ePTFE suture is a proven method of mitral valve repair, technical challenges impede its widespread utilization, especially in minimally invasive cardiac surgery. In particular, it is difficult and time consuming to manipulate a suture needle with forceps through a minimally invasive opening to place the sutures for neochordal replacement. An innovative system that remotely delivers and reliably secures ePTFE suture (or any other desired suture) would dramatically improve the accessibility and clinical outcomes following neochordal implantation.

Therefore, there is a need for an efficient and precise minimally invasive surgical suturing device that enables surgeons to utilize a minimal invasive entry point for neochordal replacement without sacrificing suturing effectiveness.

SUMMARY

A surgical suturing device is disclosed. The surgical suturing device has a forked guide tip having a plurality of legs, wherein each of the plurality of legs comprises a proximal end, an anatomical variation, and a distal end. A method of chord replacement for a heart valve is also disclosed. A suture is placed in a papillary muscle using a surgical suturing device having a forked guide tip and a papillary suture. A leaflet suture is placed in a leaflet. The papillary suture and the leaflet suture are loaded in a suture fastener from opposite directions in a coaxial fashion. The length of the papillary suture and/or the leaflet suture are adjusted relative to the suture fastener to achieve a desired replacement chord length. The suture fastener is attached to the papillary suture and the leaflet suture to lock the desired replacement chord length.

BRIEF DESCRIPTION OF THE DRAWINGS

FIGS. 4A-4E show top, front, bottom, left side, and right side views, respectively for one embodiment of a forked guide tip for a surgical suturing device.

FIGS. 6A-6C illustrate, in partial cross-sectional view, an example of using one embodiment of a surgical suturing device to place a stitch in tissue, for example, a papillary muscle.

FIGS. 7A-1 to 7G illustrate a method of using an embodiment of the surgical suturing device from FIG. 2 to place a suture in a papillary muscle.

Figure 1:
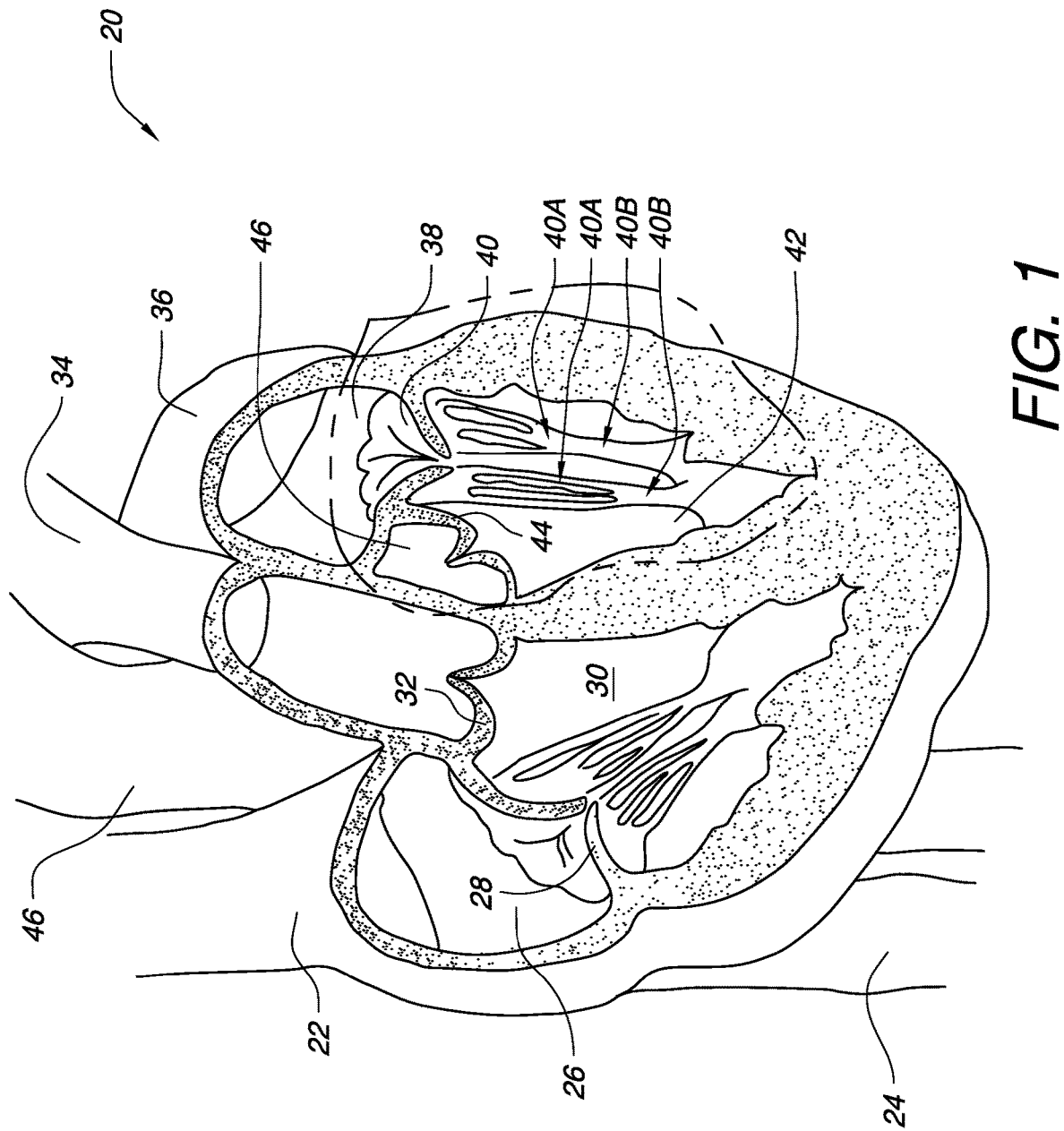
FIG. 1 is a cross-sectional view of a heart, illustrating the chambers and valves which function therein.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

Figure 2:
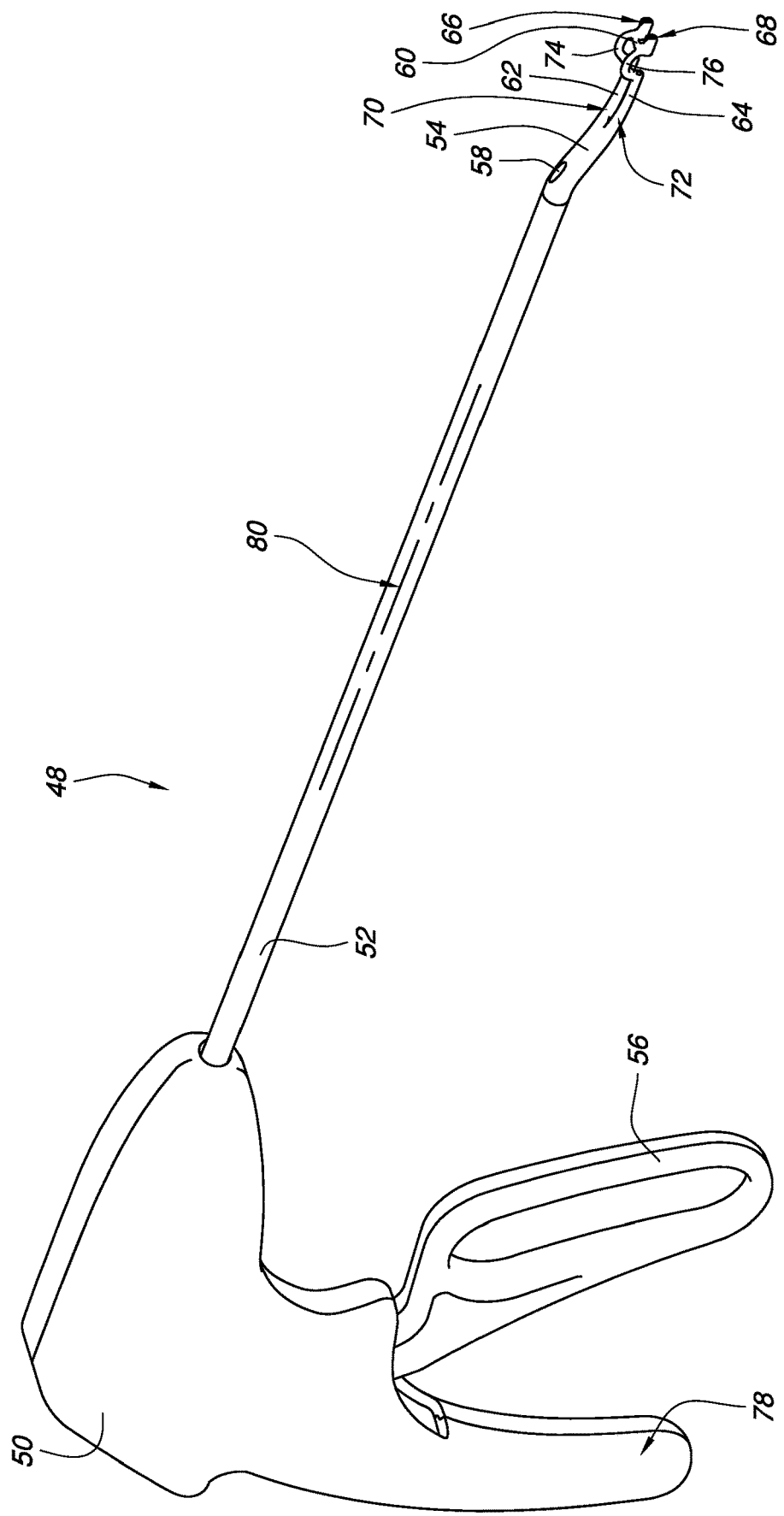
FIG. 2 is a perspective view of one embodiment of a surgical suturing device.

FIG. 2 is a perspective view of one embodiment of a surgical suturing device 48. The surgical suturing device 48 may have a housing 50 coupled to a shaft 52. A forked guide tip 54 is coupled to an end of the shaft 52, opposite from the housing 48. In some embodiments, the forked guide tip 54 may be continuous with the shaft 52, rather than a separate assembly piece which is coupled to the shaft 52. The surgical suturing device 48 also has a needle actuator 56 which is configured to move two needles (not visible in this view) within the forked guide tip 54 as will be described in greater detail below. Depending on the embodiment, some non-limiting examples of suitable shafts include a straight shaft (as illustrated), a curved shaft, a bent shaft, a flexible shaft, and an articulating shaft. Also depending on the embodiment, some non-limiting examples of suitable needle actuators include a handle (as illustrated), a lever, a knob, a slide, a gear, a wheel, a motor, and a solenoid.

Depending on the embodiment, the forked guide tip 54 may have a suture feed opening 58 which can be used to allow a portion of a suture (not shown in this view) to be loaded into at least a portion of the shaft 52 and potentially into and/or out of the housing 50 for the purpose of simplifying suture management. The forked guide tip 54 may also have one or more cross-supports 60 extending between individual legs 62, 64 of the forked guide tip 54. A distal end 66, 68 of each leg 62, 64, respectively, of the forked guide tip 54, includes a ferrule receiving aperture in alignment with a needle path (not shown in this view, but illustrated farther below) extending from proximal portions 70, 72 of the respective forked guide tip legs 62, 64.

Between the proximal and distal ends 70, 66 of the forked guide tip leg 62, the fork leg 62 includes an anatomical variation 74. Similarly, the other forked guide tip leg 64 has an anatomical variation 76 between its proximal and distal ends 72, 68. The anatomical variations 74, 76 are sized to help guide the forked guide tip 54 onto one or more anatomical structures. In the illustrated embodiment, the anatomical variations 74, 76 include arches sized and shaped to fit on a papillary muscle. The openings between the forked legs 62, 64 help to provide visibility to tissue when the anatomical variations are positioned by a surgeon operating the device, for example by manipulating the housing 50 with the attached handle 78. The forked legs 62, 64 may also be curved away from a longitudinal axis 80 of the shaft 52 to provide added visibility through the forked area. In a preferred embodiment, the forked legs 62, 64 are curved in a concave fashion with respect to the longitudinal axis 80 passing over them as illustrated in FIG. 2.

Figure 3:
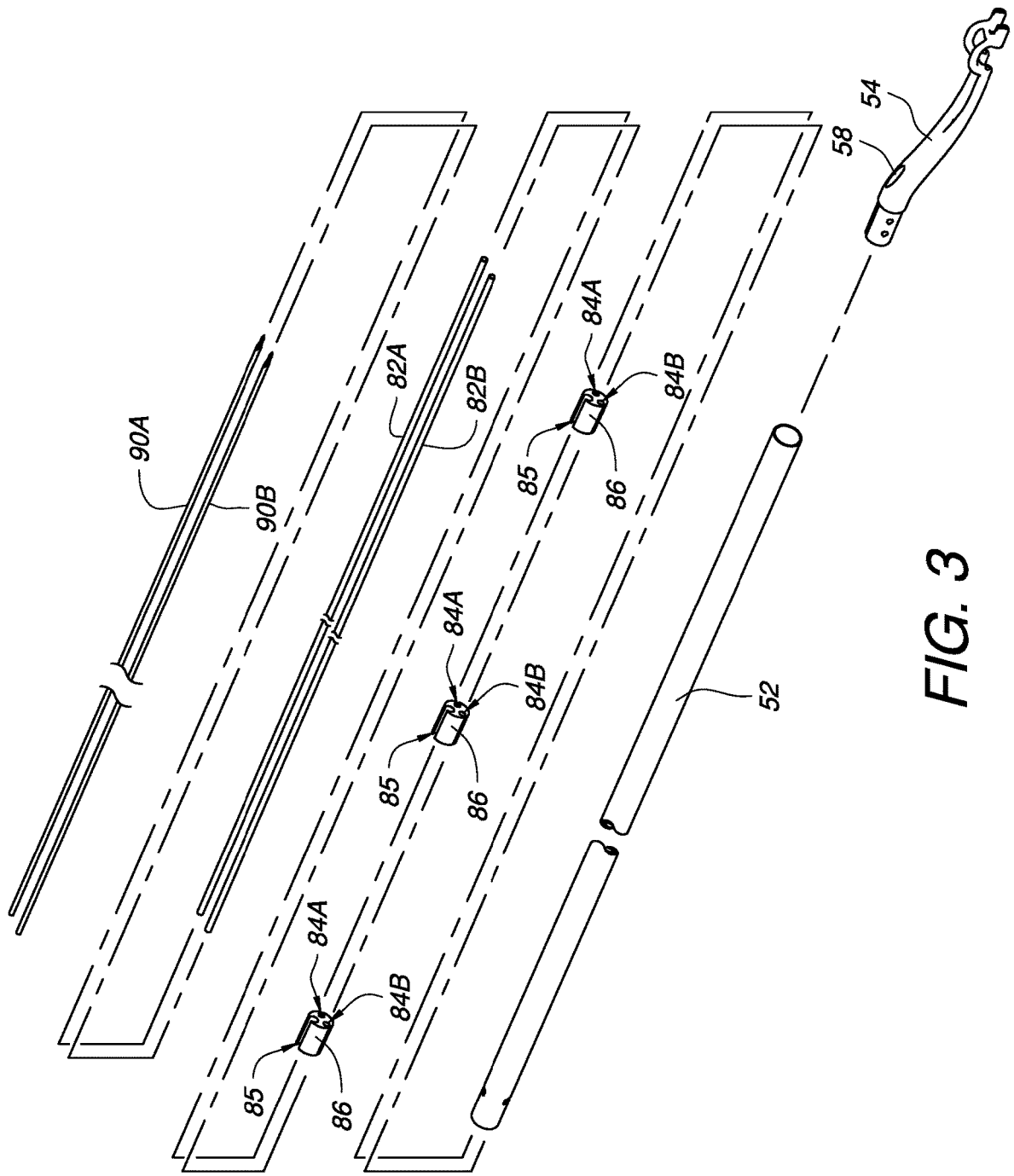
FIG. 3 is an exploded perspective view of the embodied surgical suturing device of FIG. 2 without the housing or needle actuator.

FIG. 3 is an exploded perspective view of the embodied surgical suturing device of FIG. 2 without the housing 50 or needle actuator 56. Two needle guide tubes 82A, 82B are inserted into respective openings 84A, 84B in multiple supports 86. The supports 86 may be distributed evenly or unevenly along the guide tubes 82A, 82B. The shaft 52 is hollow and the supports 86 are sized to fit into and be supported by the inside of the shaft 52. The forked guide tip 54 attaches to the distal end 88 of the shaft 52 such that the needle guide tubes 82A, 82B align with needle channels (not visible in this view, but discussed below and shown in FIGS. 4A-4E) in the forked guide tip 54. Two needles 90A, 90B can be inserted into respective needle guide tubes 82A, 82B as illustrated in FIG. 3. The supports 86 can also include a suture passage 85 to allow a portion of a suture (not shown in this view), fed into the shaft 52 via the suture feed opening 58, to extend either partially into the shaft 52 or all the way through the shaft 52 and into the housing 50 (not shown in this view).

FIGS. 4A-4E show top, front, bottom, left side, and right side views, respectively for one embodiment of a forked guide tip 54 for a surgical suturing device. The needle channels 92A, 92B can be seen passing from the proximal end 94 of the guide tip 54 through the respective legs 62, 64 of the forked guide tip 54. The distal ends 66, 68 of the legs 62, 64 each have a respective ferrule receiving aperture 96A, 96B which will be discussed in more detail further in this specification. The suture feed opening 58 can be seen extending through the forked guide tip 54 towards and all the way through the proximal end 94 of the forked guide tip 54. The cross supports 60 and the anatomical variations 74, 76 discussed previously, are also shown in one or more views of FIGS. 4A-4E.

FIGS. 4A-4E show top, front, bottom, left side, and right side views, respectively for one embodiment of a forked guide tip 54 for a surgical suturing device as described above.

Figure 5:
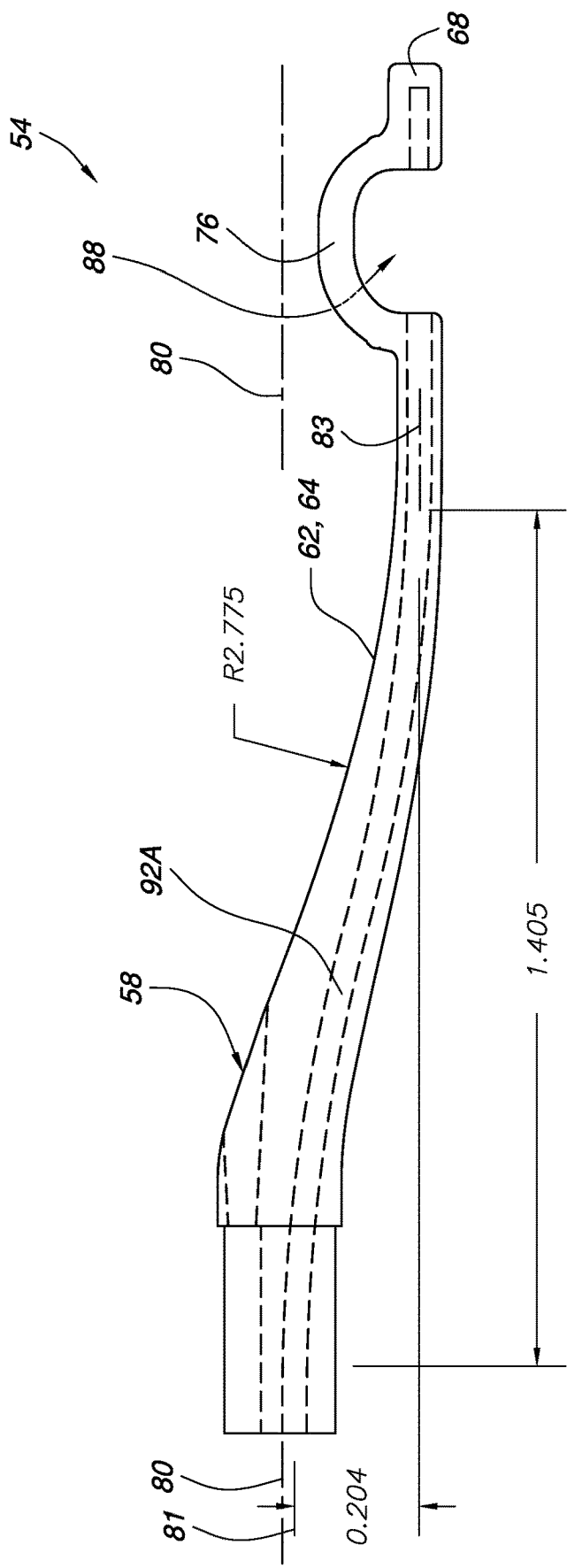
FIG. 5 illustrates the forked guide tip of FIG. 4B with one non-limiting embodiment of advantageous and ergonomic dimensions.

Various embodiments of a forked guide tip can be manufactured with a wide range of dimensions. As one non-limiting example, FIG. 5 illustrates a forked guide tip 54 with one non-limiting embodiment of advantageous and ergonomic dimensions. In the embodiment of FIG. 5, the legs 62, 64 have a substantially concave shape with respect to the longitudinal axis 80 of the shaft. The needle channel 92A has a proximal channel axis 81 which us approximately 0.204 inches above a tip axis 83. The proximal channel axis 81 and the tip axis 83 are substantially parallel. The portion of the needle channel 92A corresponding to the proximal channel axis and the portion of the needle channel 92A corresponding to the tip axis 83 are approximately 1.405 inches apart when measured in a direction parallel to the proximal channel axis 81. The upper curve R2 of the legs 62, 64 has a radius of approximately 2.775 inches.

FIGS. 6A-6C illustrate, in partial cross-sectional view, an example of using one embodiment of a surgical suturing device to place a stitch in tissue, for example, a papillary muscle 108. Although the side view illustrates only a single leg 62, it should be understood that there is a second leg not visible in this view that functions similarly to the shown leg. The anatomical variation 74, in conjunction with the end of the leg 62 near the anatomical variation 74 and the distal end 112 of the device form a tissue bite area 98 which may be placed over the tissue in question (in this example, a papillary muscle 108). The distal end 112 has a ferrule receiving aperture 96A into which a ferrule 100 has been positioned. The ferrule 100 is coupled to a suture 102 which exits from a slot in the distal end 112 of the device. Depending on the embodiment, the end of the suture 102 opposite the ferrule 100 may terminate in a second ferrule (not shown) that is installed in the ferrule receiving aperture of the second leg (which is not visible in this side view. In other embodiments, the end of the suture 102 opposite the ferrule 100 may have nothing attached thereto. For simplicity in the views of FIGS. 6A-6C, the suture 102 is simply shown as ending at a break line, however, in practice, part of the suture 102 can be fed back through the suture feed opening 58 to help manage the suture 102. It should be understood that the term "suture", as used herein, is intended to cover any thread, cable, wire, filament, strand, line, yarn, gut, or similar structure, whether natural and/or synthetic, in monofilament, composite filament, or multifilament form (whether braided, woven, twisted, or otherwise held together), as well as equivalents, substitutions, combinations, and pluralities thereof for such materials and structures.

With reference to FIG. 6A, a needle 90A is positioned within needle channel 92A in a refracted position. The needle 90A has a ferrule-engaging tip 106 which is also configured to be able to penetrate tissue 108. In FIG. 6B, an actuator (not shown), coupled to the needle 90A, moves the needle 90A in a distal direction 110, causing the ferrule engaging tip 106 to penetrate the tissue 108 in the tissue bite area 98 as it moves across the tissue bite area 98 and then engages the ferrule 100 held by the ferrule receiving aperture 96A. In FIG. 6C, the actuator moves the needle 90A in a proximal direction 114, causing the ferrule-engaging tip 106 and the ferrule 100 which is attached to it to be pulled back across the tissue bite area 98 and through the tissue 108. A portion of the suture 102 is also pulled back through the tissue 108.

Figures 1, 7A:
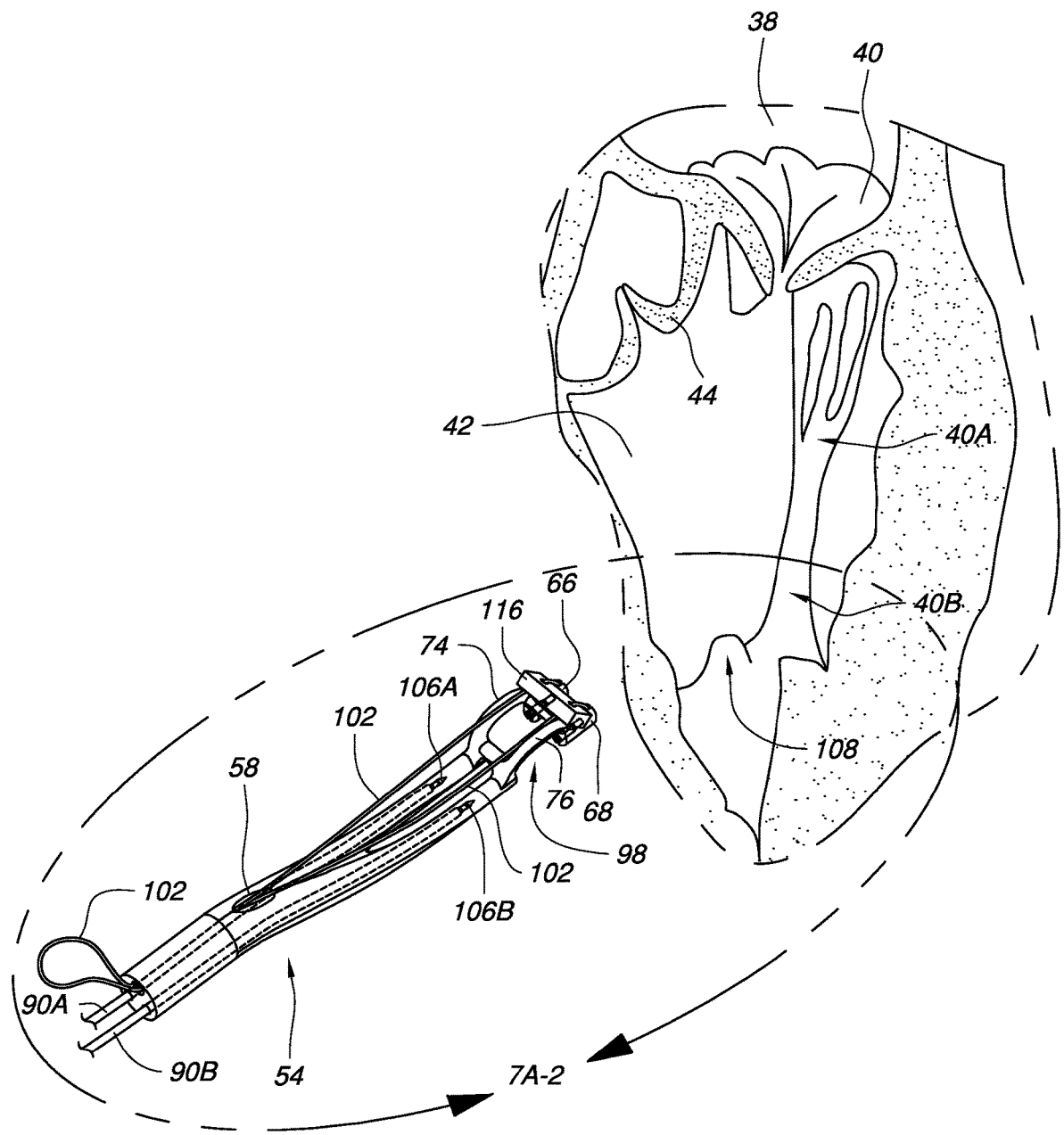
Figures 2, 7A:
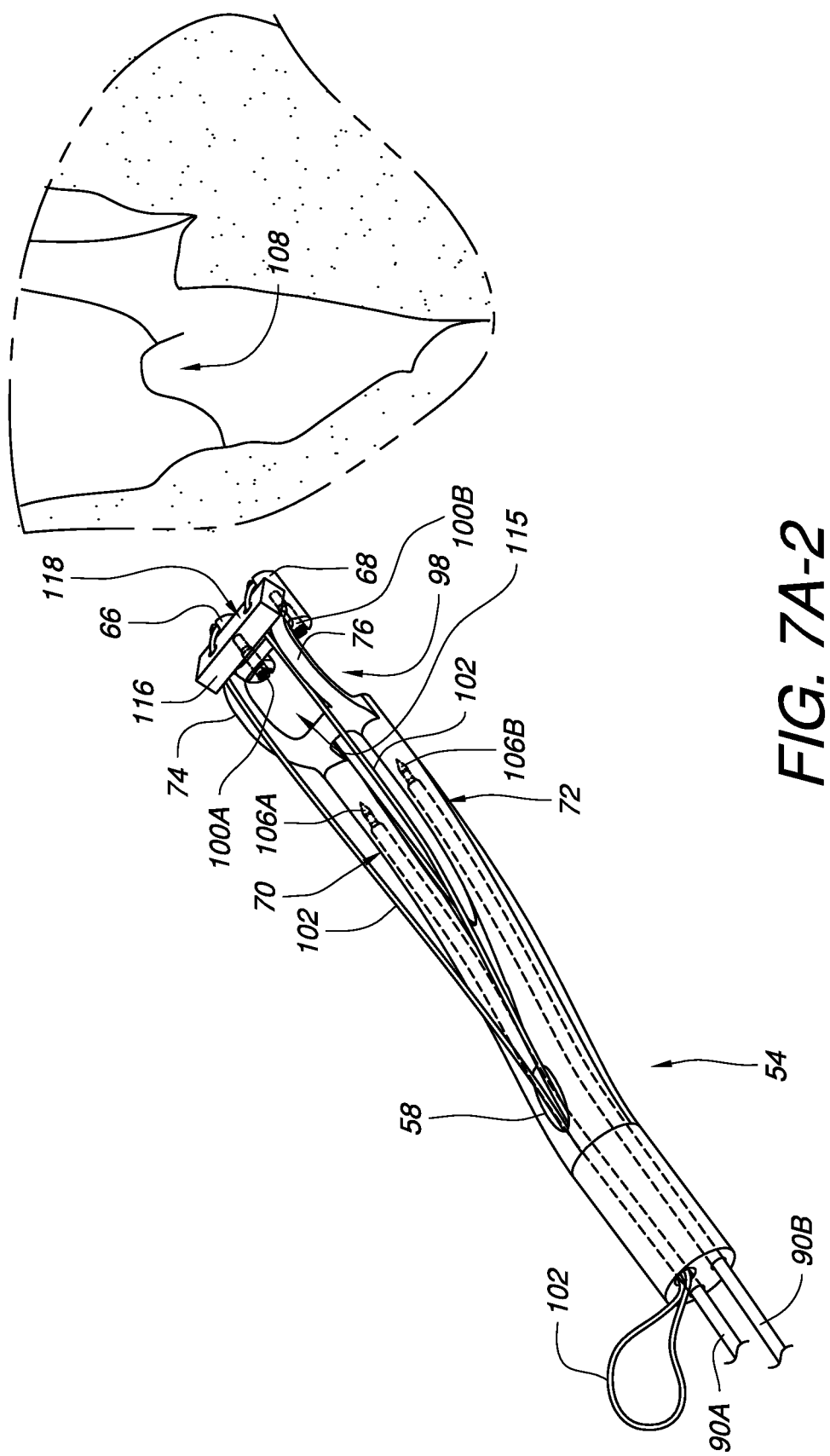
Figure 7B:
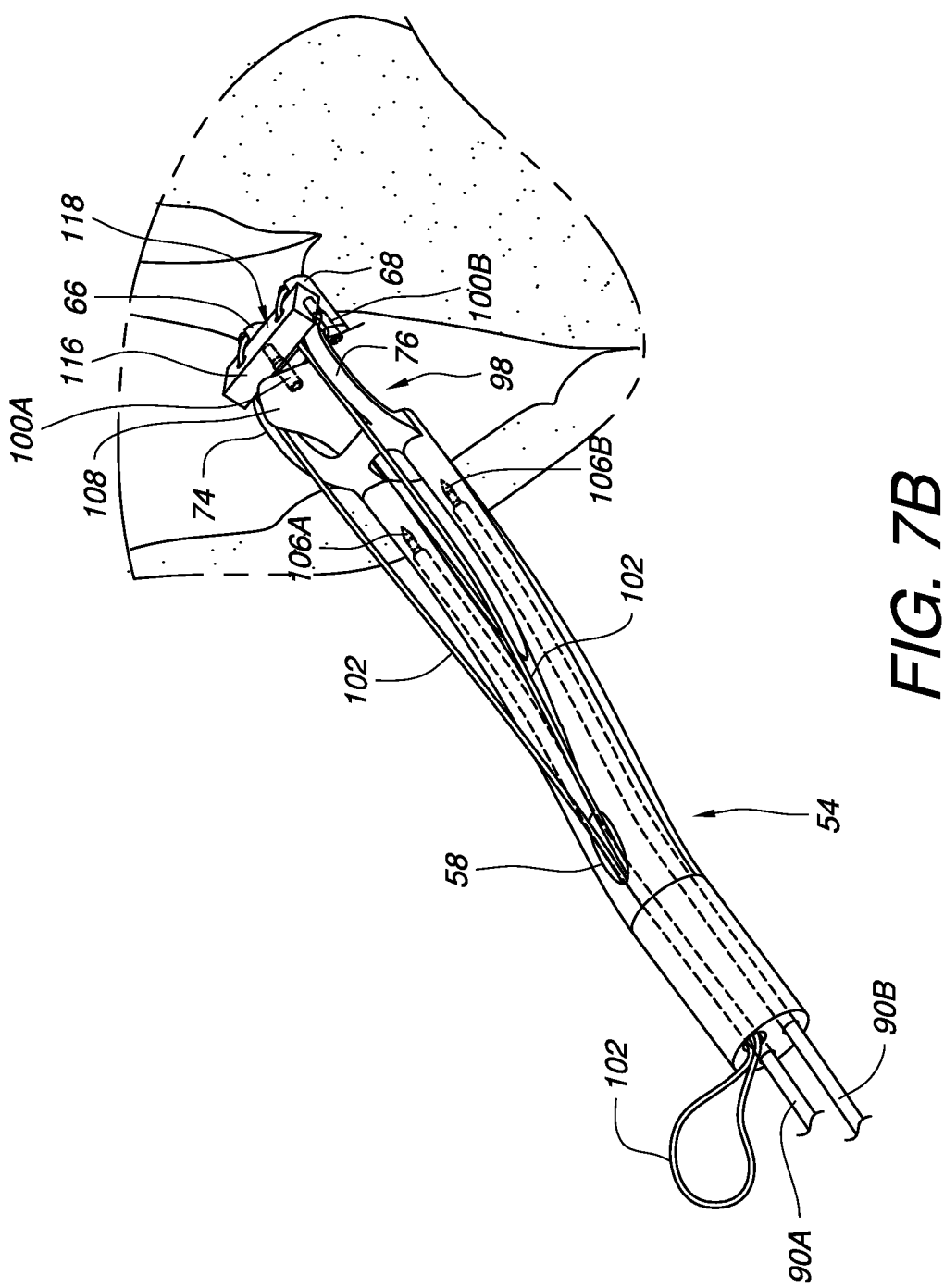
Figure 7C:
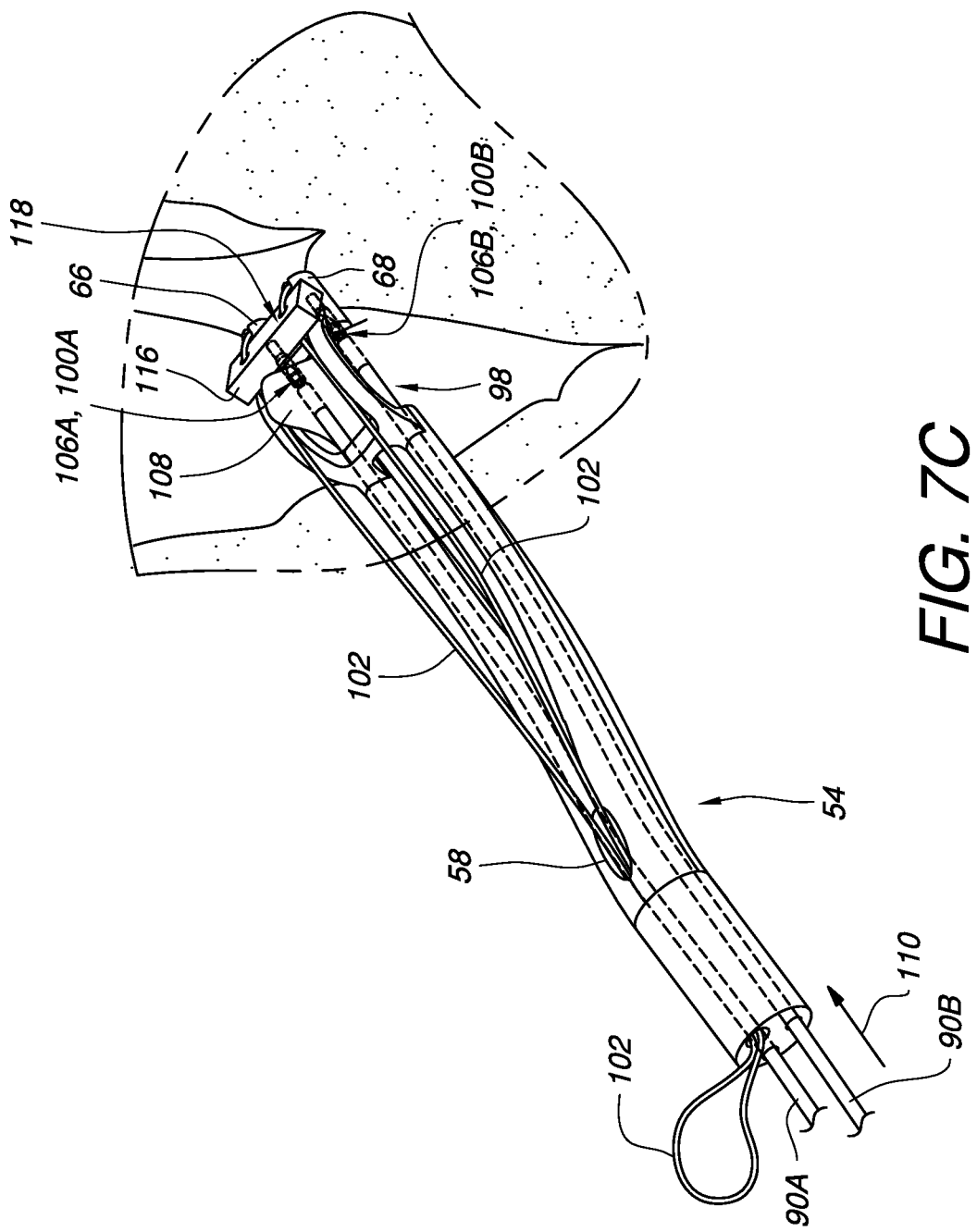
Figure 7D:
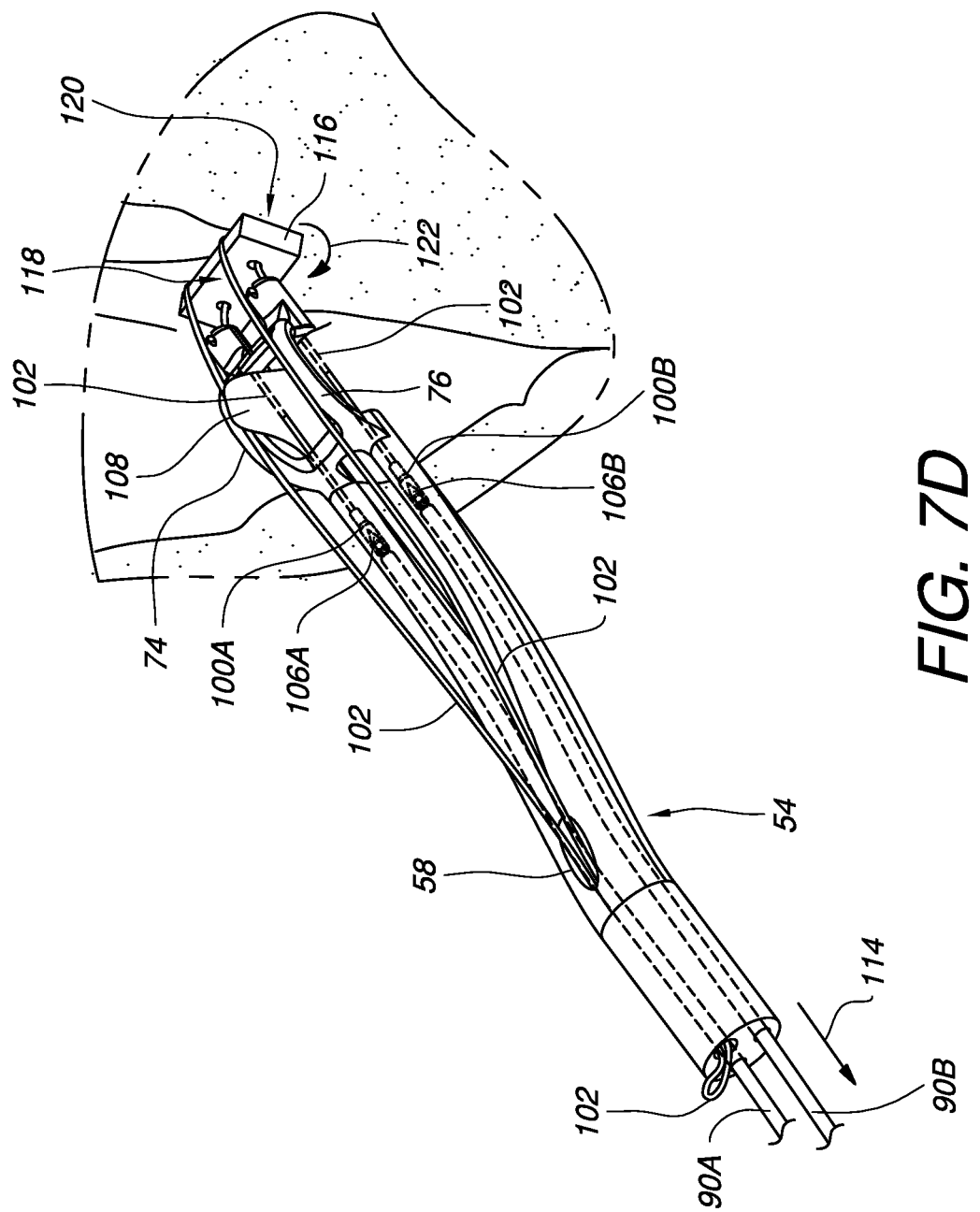
Figure 7E:
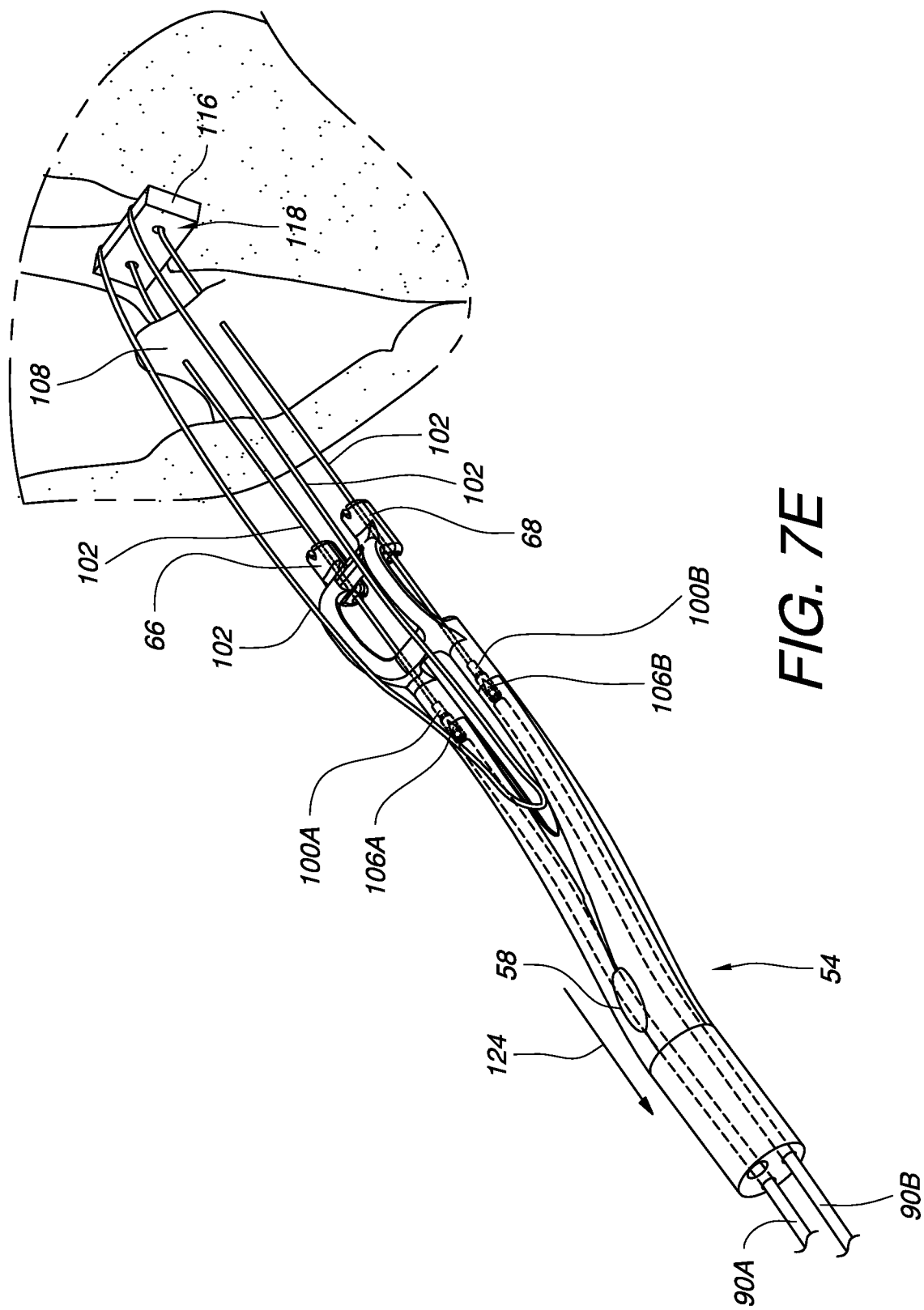
Figure 7F:
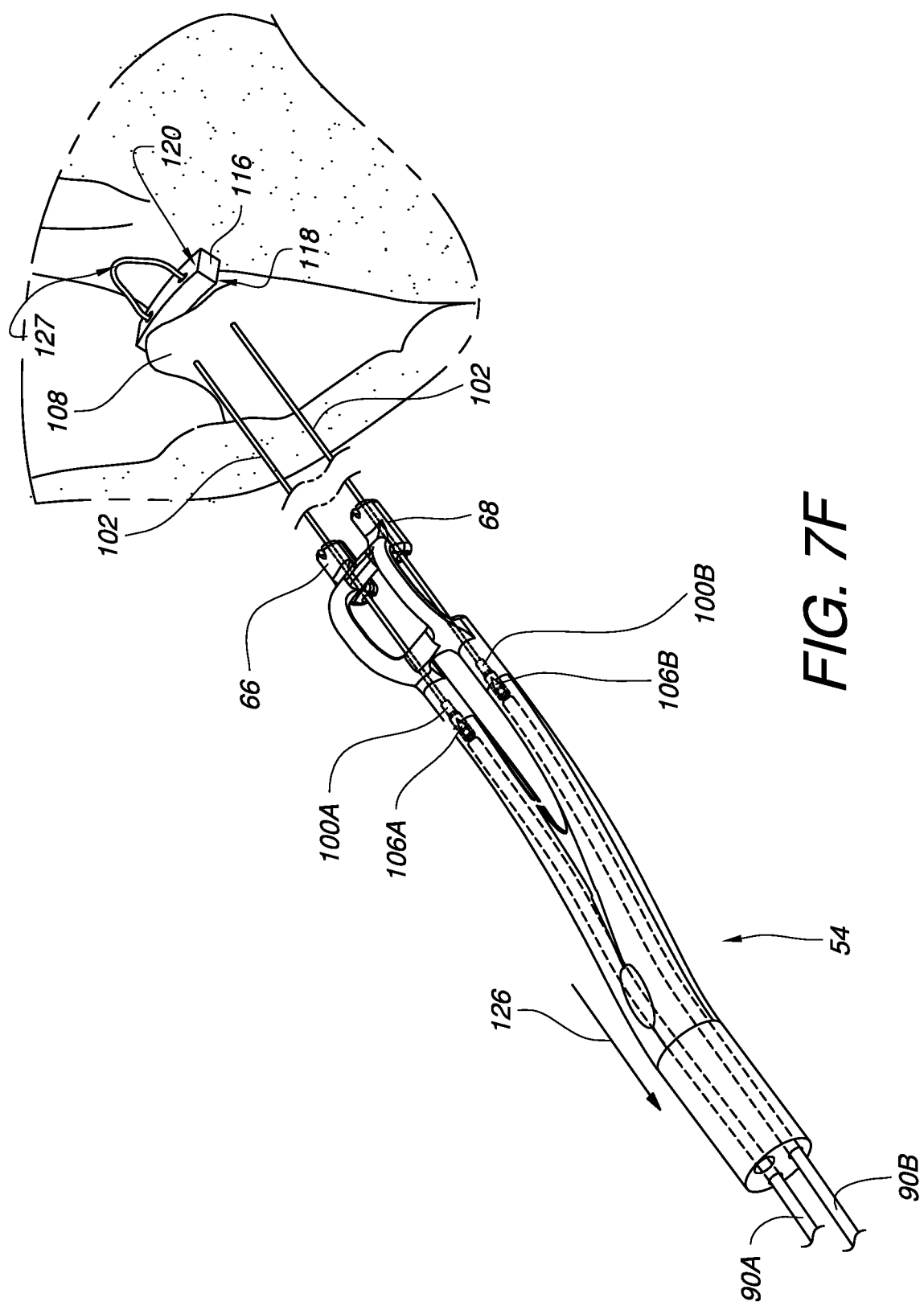
Figure 7G:
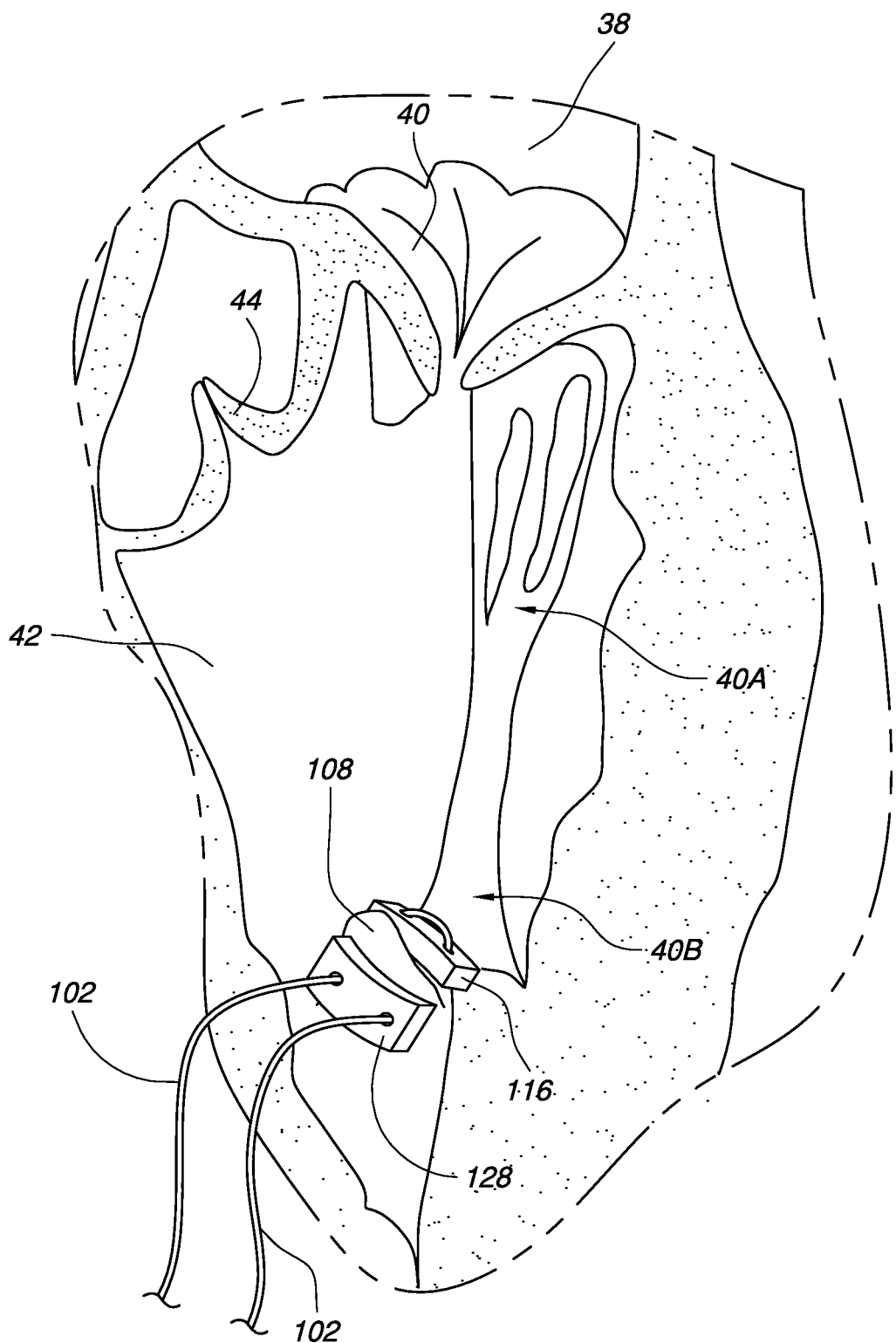

The utility of such a device and its equivalents is further illustrated with respect to the perspective views of FIGS. 7A-1 to 7G which better show the dual needles 90A, 90B in action. FIGS. 7A-1 to 7G illustrate a method of using an embodiment of the surgical suturing device from FIG. 2 to place a suture 102 in a papillary muscle 108. FIG. 7A-1 schematically illustrates a surgical situation. Minimally invasive access has been gained to the left ventricle 42 of the heart. Healthy chordae 40A are coupled between a papillary muscle 40B and leaflets of the mitral valve 40. A pathologic chord has been removed from another papillary muscle 108 and the suturing device is ready to be used. For convenience the shaft, handle, and actuator of the surgical device are not illustrated in these views.

The suturing device and the papillary muscle 108 may be seen more clearly in the enlarged view of FIG. 7A-2. As before, the device has a forked guide tip 54 having first and second legs. The first leg has a proximal end 70, an anatomical variation 74, and a distal end 66. The second leg has a proximal end 72, an anatomical variation 76, and a distal end 68. The device also has a viewing area 115 defined at least in part by the anatomical variations 74, 76 of the forked guide tip 54. A first needle 90A, having a suture engaging tip 106A, resides in the first leg in a refracted position. A second needle 90B, having a suture engaging tip 106B, resides in the second leg in a retracted position. A first ferrule 100A is held in the distal end 66 of the first leg, while a second ferrule 100B is held in the distal end 68 of the second leg. A suture 102 runs from the first ferrule 100A, through a first hole in a pledget 116, back into the suture feed opening 58, reverses back out of the suture feed opening 58, through a second hole in the pledget 116, and to the second ferrule 100B. In this embodiment, the pledget 116 rests on part of one or more of the anatomical variations 74, 76. In other embodiments, the pledget 116 may rest on other portions of the device. The pledget 116 has a first face 118 where the end of suture 102 exit the pledget 116 to couple to the ferrules 100A, 100B.

As illustrated in FIG. 7B, the tissue bite area 98 is placed over the papillary muscle 108. This can advantageously be done by looking through the viewing area 115 from FIG. 7A-2. As illustrated in FIG. 7C, the first and second needles 90A, 90B are moved by the actuator (not shown) in a distal direction 110, causing the ferrule engaging tips 106A, 106B to penetrate the tissue 108 in the tissue bite area 98 as they move across the tissue bite area 98 and then engage the respective ferrules 100A, 100B held in the distal ends 66, 68. In FIG. 7D, the actuator (not shown) moves the needles 90A, 90B in a proximal direction 114, causing the ferrule-engaging tips 106A, 106B and the respective ferrules 100A, 100B which are attached to them to be pulled back through the tissue 108. Portions of the suture 102 are also pulled back through the tissue 108. As the suture 102 is pulled through the tissue 108, the pledget 116 may start to pivot 122 off the end of the device so that the first side 118 of the pledget 116 starts to face the tissue 108. A second side 120 of the pledget 116 is located opposite the first side 118 of the pledget 116. As the suture 102 is pulled back through the tissue 108, the suture 102 starts to play out of the suture feed opening 58.

In FIG. 7E, the suturing device is pulled away 124 from the papillary muscle 108 and the suture 102 may exit the suture feed opening 58 completely. As illustrated in FIG. 7F, the device may continue to be withdrawn 126 such that the first side of the pledget 118 contacts the tissue 108 as the approximate midpoint 127 of the suture 102 is pulled against the second side 120 of the pledget 116. The ferrules 100A, 100B held by the device may then be removed from the ends of the suture 102. While other embodiments may not use a pledget 116, the pledget does provide an advantageous interface to help protect the suture stitch from pulling through the tissue. In fact, in some embodiments, the suture ends passing out of the tissue 108 may be threaded through a second pledget 128 so both sides of the papillary muscle are pledgeted as illustrated in FIG. 7G.

Figure 7H:
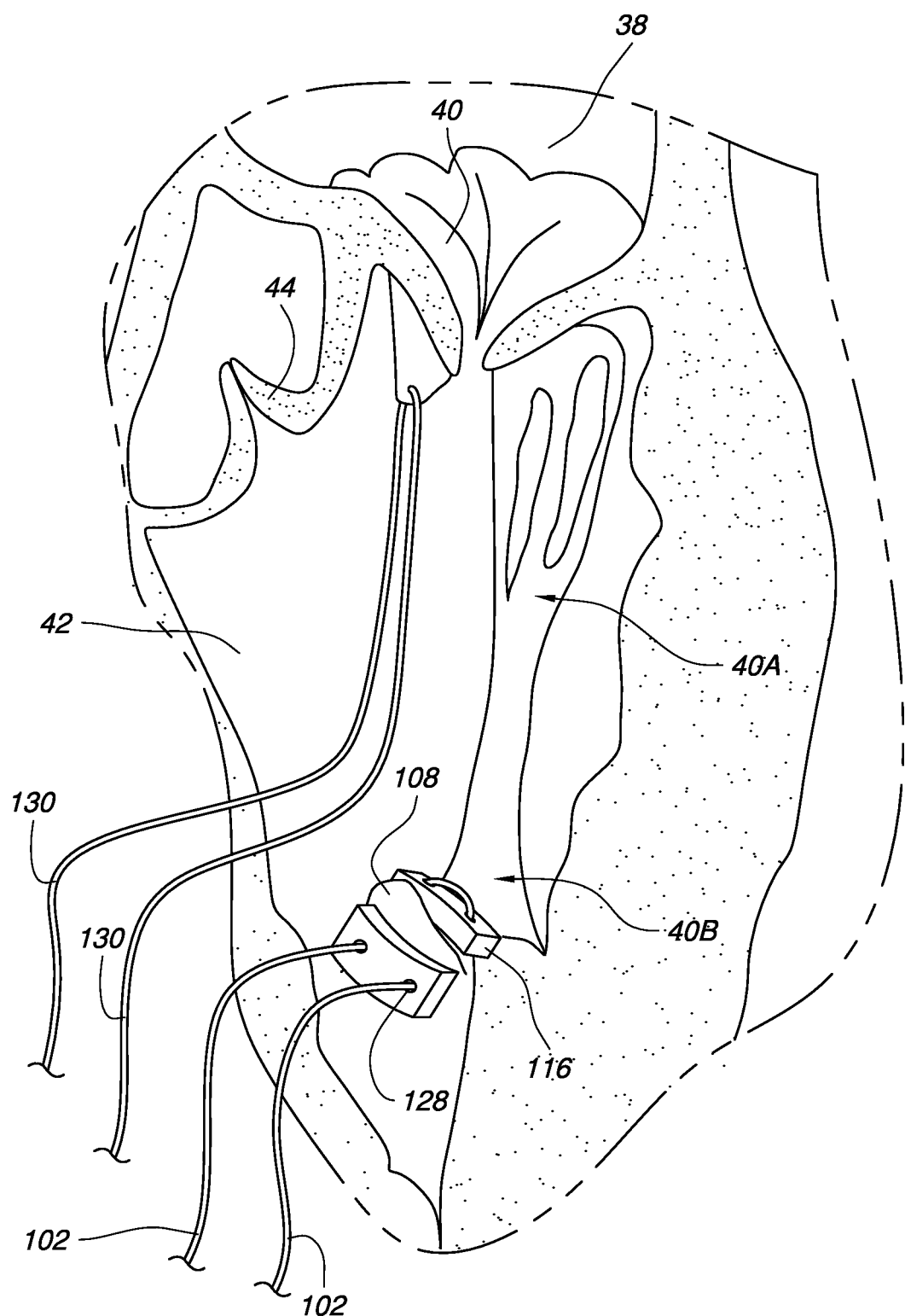
FIGS. 7H-7I illustrate a method of coupling a first suture placed in a papillary muscle and a second suture placed in a valve leaflet to each other using a mechanical fastener to replace a chordae tendinae of the heart.
Figure 7I:
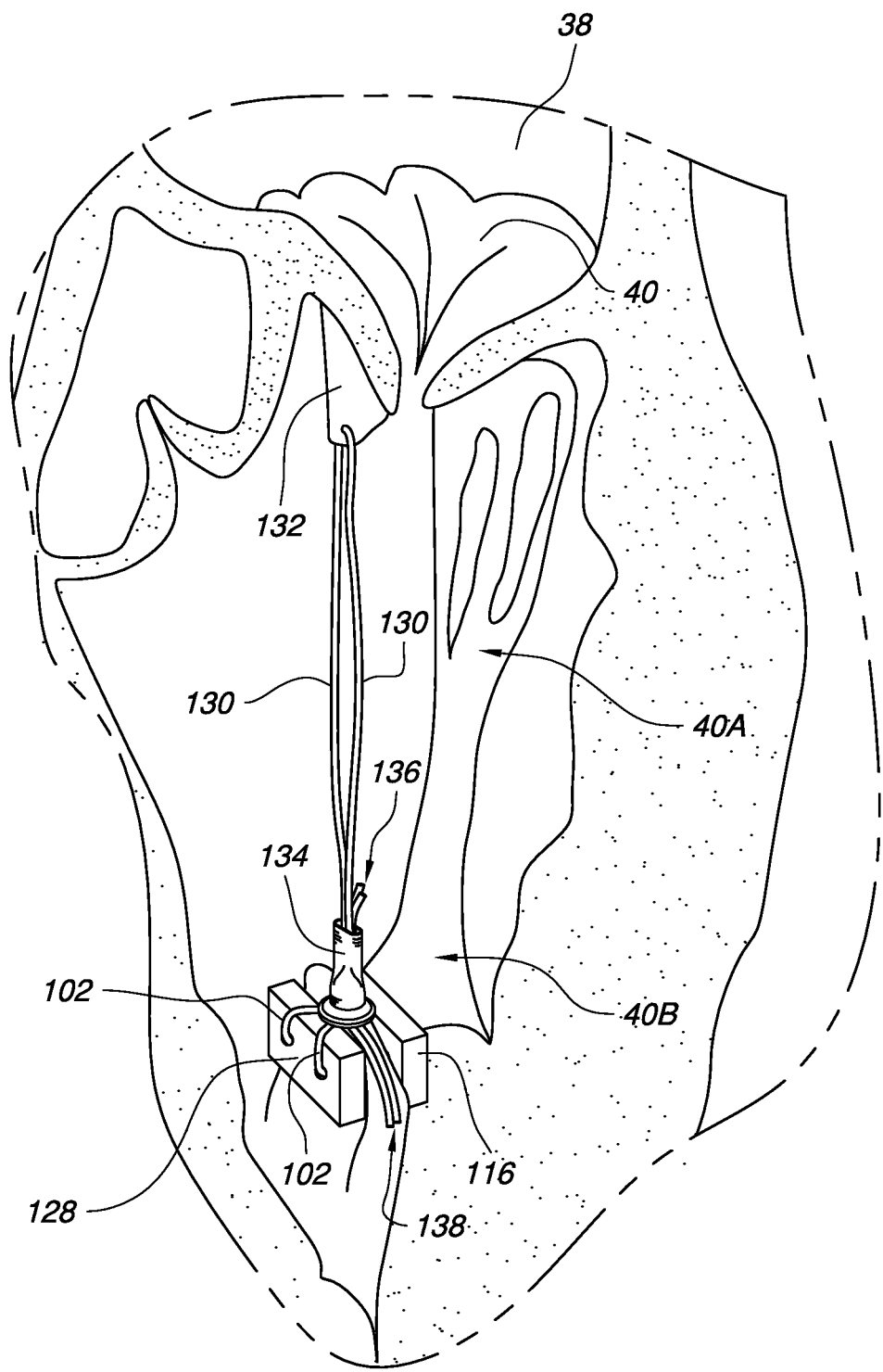

FIGS. 7H-7I illustrate a method of coupling a first suture 102 placed in a papillary muscle 108 (for example, as illustrated in the method of FIGS. 7A-2 to 7G) and a second suture 130 placed in a valve leaflet 132 to each other using a mechanical fastener to replace a chordae tendinae of the heart. FIG. 7H simply shows the second suture 130 after it has been stitched through a leaflet 132 of the mitral valve 40. Those skilled in the art will be familiar with a variety of ways to create this stitch of the second suture 130. FIG. 7I illustrates a mechanical fastener 134 which has been fastened to hold a first set of suture ends 136 of the first suture 102 which have been passed up through the mechanical faster 134. The mechanical fastener 134 also holds a second set of suture ends 138 of the second suture 130 which have been passed down through the mechanical fastener 134. One suitable method for fastening the two sets of suture ends together in this fashion is disclosed in U.S. Patent Application Publication 2014/0276979, published Sep. 18, 2014 for U.S. patent application Ser. No. 13/840,481 filed Mar. 15, 2013, the entirety of which is hereby incorporated by reference.

Figure 8:
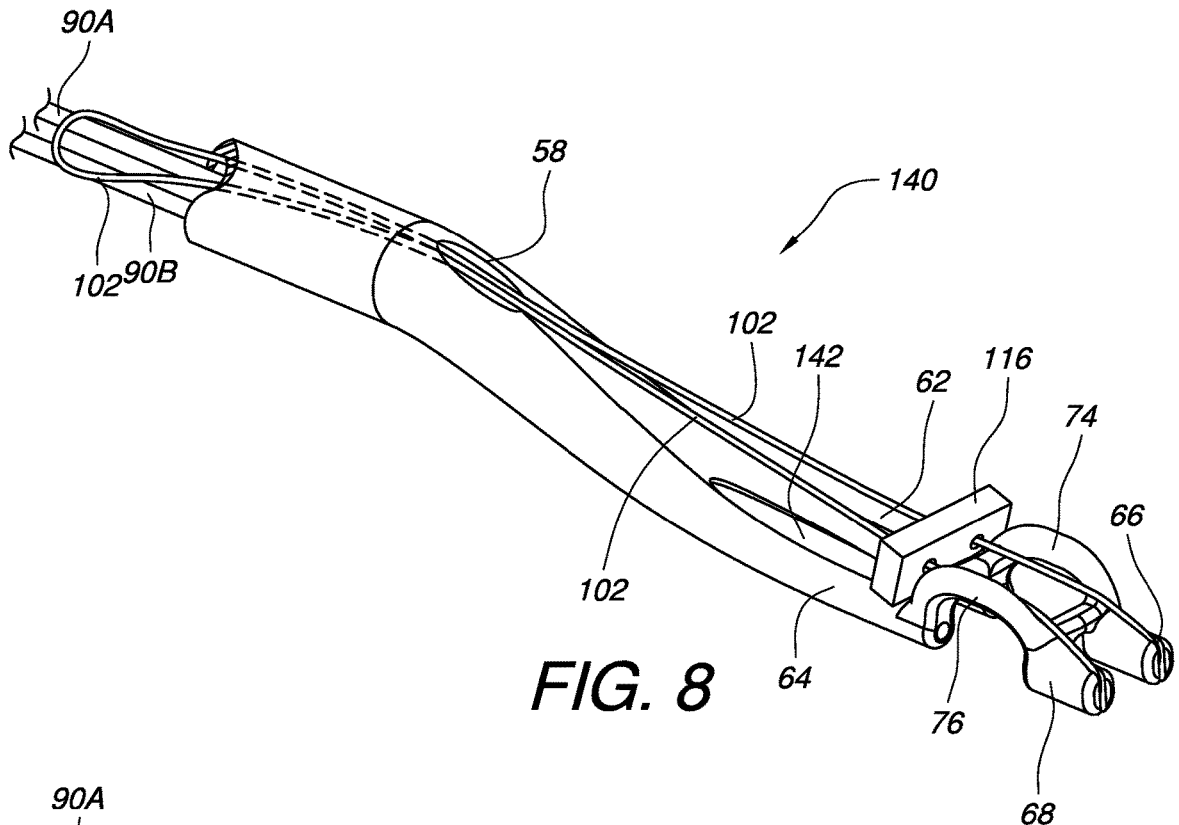
FIGS. 8 and 9 illustrate alternate embodiments for using the forked guide tip of FIG. 2 with a pledgeted suture.
Figure 9:
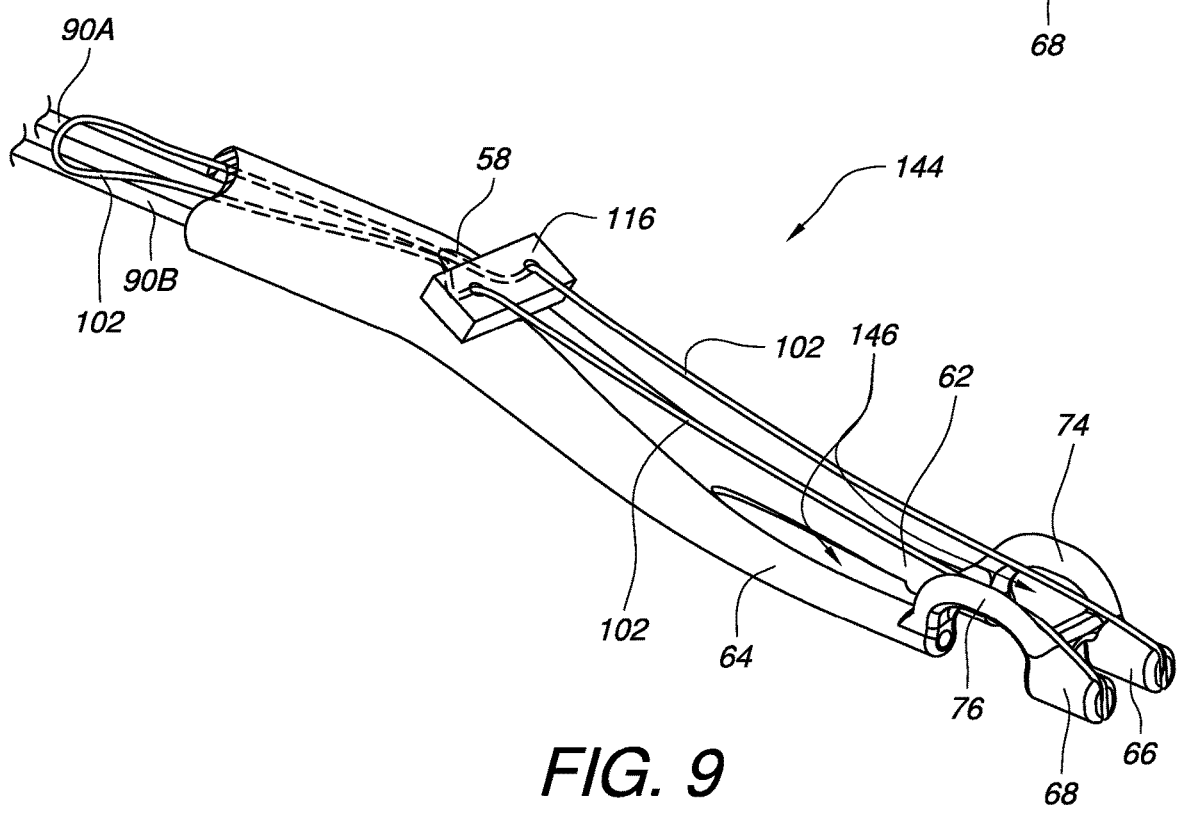

FIGS. 8 and 9 illustrate alternate embodiments for using the forked guide tip of FIG. 2 with a pledgeted suture. The forked guide tip 140 embodiment of FIG. 8 is similar to previous embodiments, except for the pledget 116 which is rested against a proximal side of the anatomical variations 74, 76. In this embodiment, the viewing area 142 is defined between the forked legs 62, 64 and the proximal portions of the anatomical variations 74, 76. The forked guide tip embodiment of FIG. 9 is similar to previous embodiments, except for the pledget 116 which is rested against the suture feed opening 58. In this embodiment, the viewing area 146 is potentially much larger without the pledget 116 blocking a portion of the view.

Figure 10A:
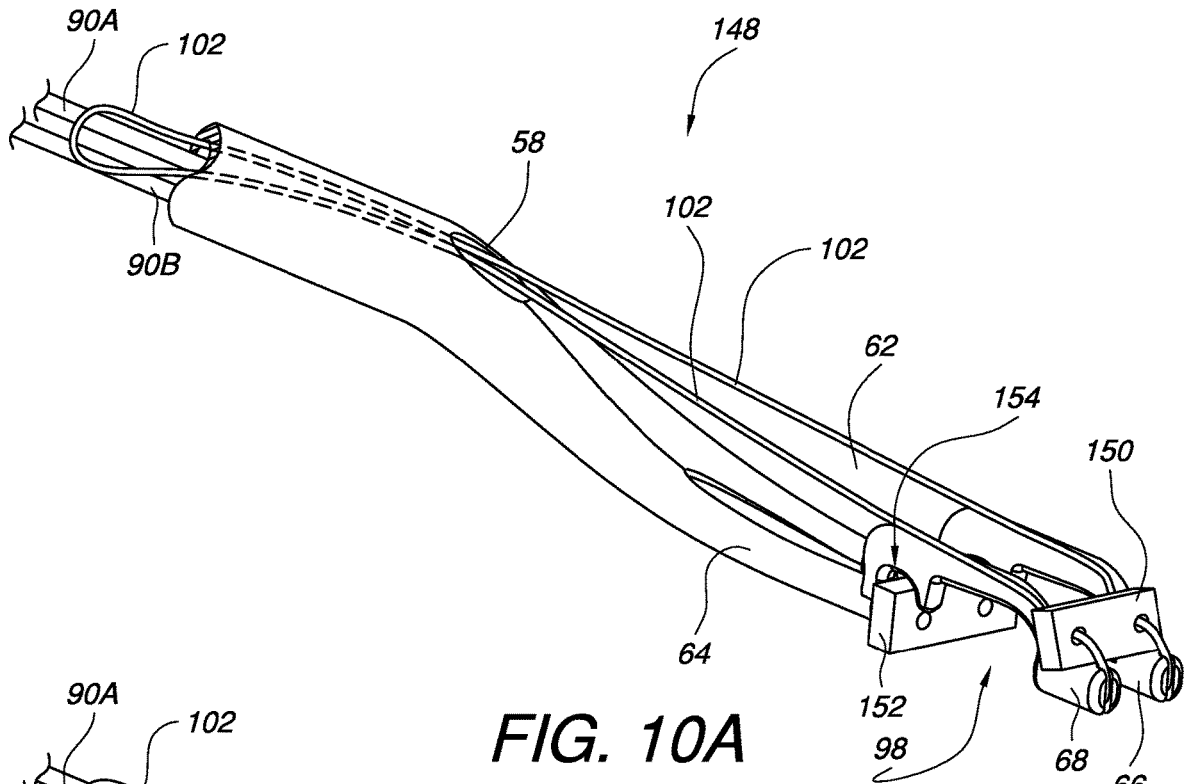
FIGS. 10A-10B illustrate one embodiment of a forked guide tip for a surgical suturing device for placing a double-pledgeted suture in a papillary muscle.
Figure 10B:
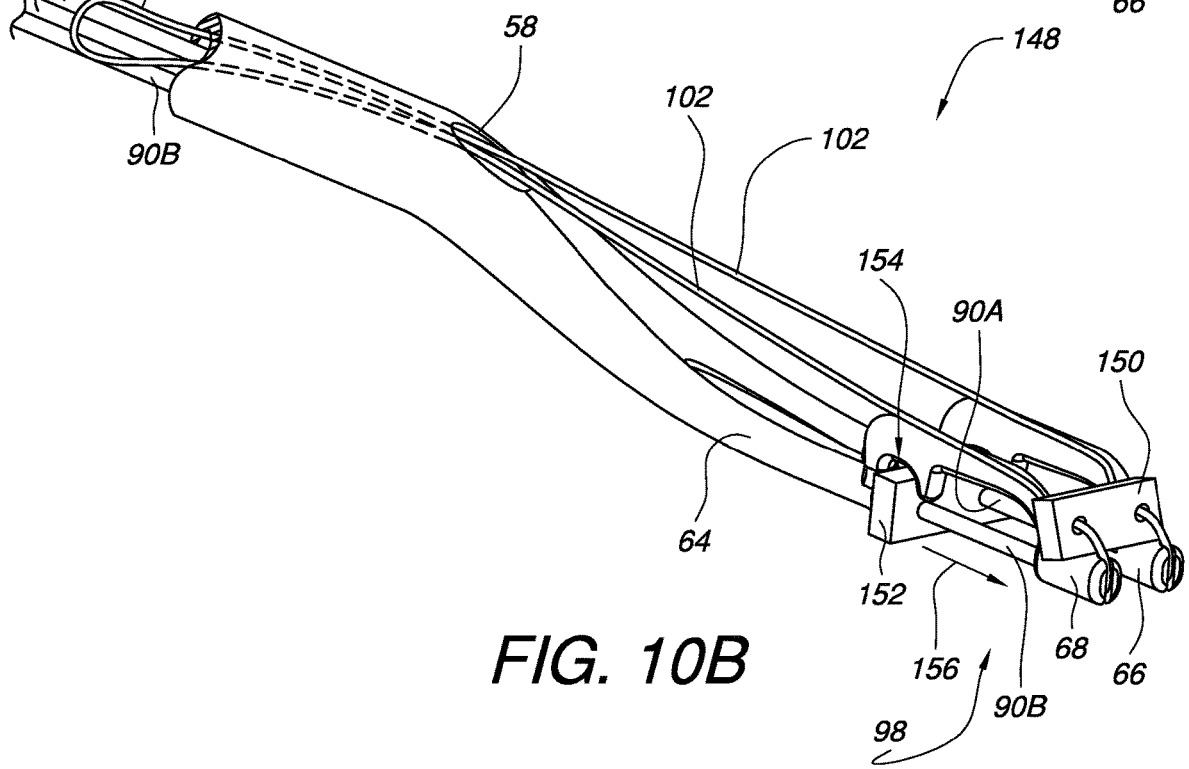

FIGS. 10A-10B illustrate one embodiment of a forked guide tip 148 for a surgical suturing device for placing a double-pledgeted suture in a papillary muscle. The forked guide tip 148 is similar to previous embodiments in that it includes a first pledget 150 through which the suture 102 is routed before reaching the ferrules in the distal leg ends 66, 68. In this embodiment, however, a second pledget 152 is held in a pledget holder 154 adjacent to the tissue bite area 98. The second pledget 152 is preferably positioned so that the pledget holes are in alignment with the openings in the legs 62, 64 from which the needles 90A, 90B will extend. As illustrated in FIG. 10B, the needles 90A, 90B may be advanced 156 out of the legs, through the second pledget 152, across the tissue bite area 98 and into engagement with the ferrules. When the ferrules and suture are pulled back through the tissue bite area, they will then be pulled through the second pledget, thereby double-pledgeting the tissue sutured by the device.

Figure 11A:
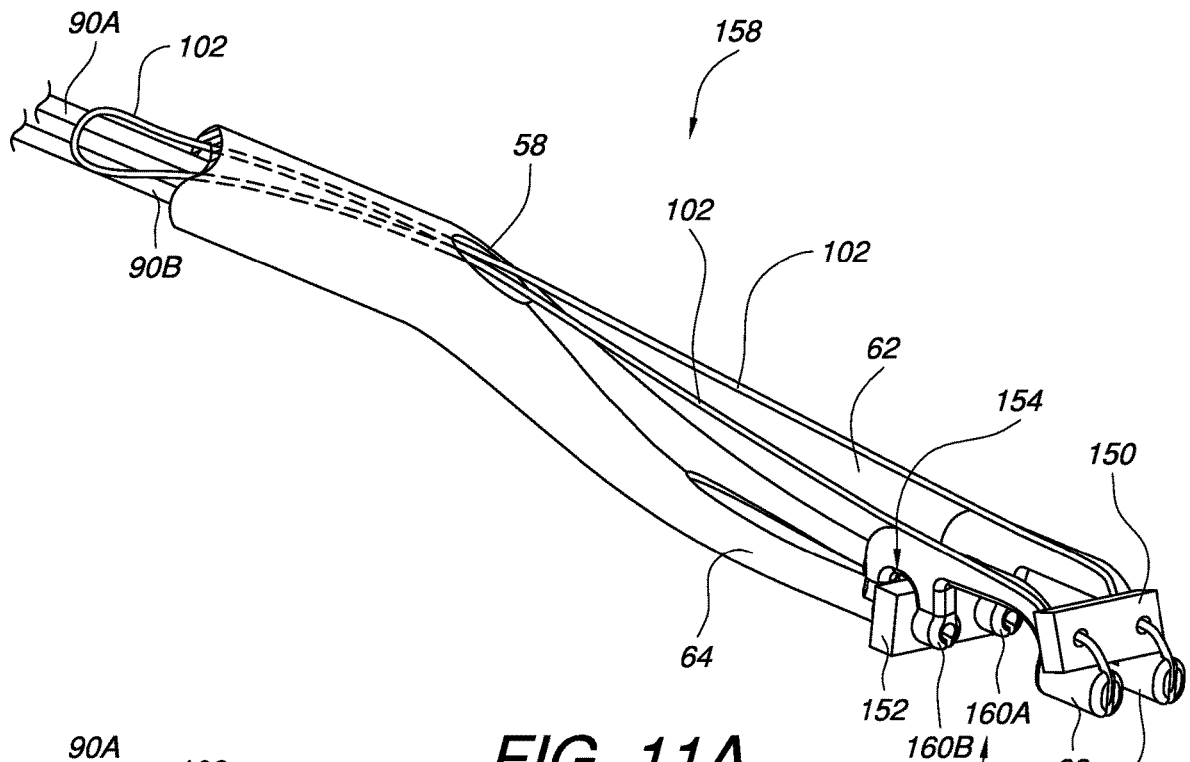
FIGS. 11A-11B illustrate another embodiment of a forked guide tip for a surgical suturing device for placing a double-pledgeted suture in a papillary muscle.
Figure 11B:
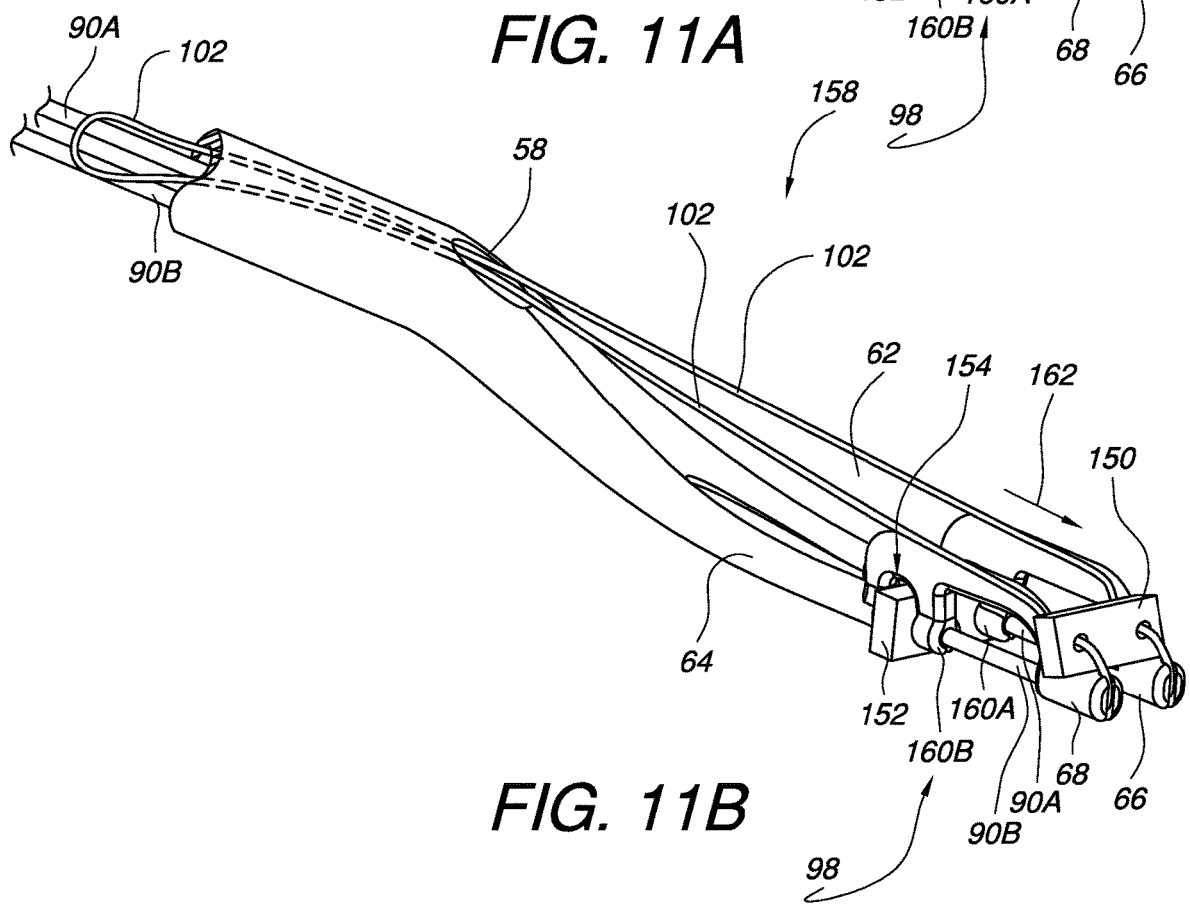

FIGS. 11A-11B illustrate another embodiment of a forked guide tip 158 for a surgical suturing device for placing a double-pledgeted suture in a papillary muscle. The forked guide tip 158 is similar to the embodiment of FIG. 10A, except that it also includes pledget hole stabilizers 160A, 160B on the tissue gap 98 side of the pledget holder 154. Since the needles 90A, 90B may tend to push the second pledget 152 out of the pledget holder 154 in some embodiments as they pass through the second pledget 152, the pledget hole stabilizers 160A, 160B may help prevent the movement of the second pledget away from the needles 90A, 90B. The pledget hole stabilizers 160A, 160B may also enable the use of a second pledget 152 which does not have pre-formed holes, since the needles 90A, 90B will be able to pierce the second pledget as it held in place by the pledget holder 154 and the pledget hole stabilizers 160A, 160B. As illustrated in FIG. 11B, the needles 90A, 90B may be advanced 162 out of the legs 62, 64, through the second pledget 152, through the pledget hole stabilizers 160A, 160B, across the tissue bite area 98 and into engagement with the ferrules held in the distal ends 66, 68. When the ferrules and suture are pulled back through the tissue bite area 98, they will then be pulled through the second pledget, thereby double-pledgeting the tissue sutured by the device.

Figure 12:
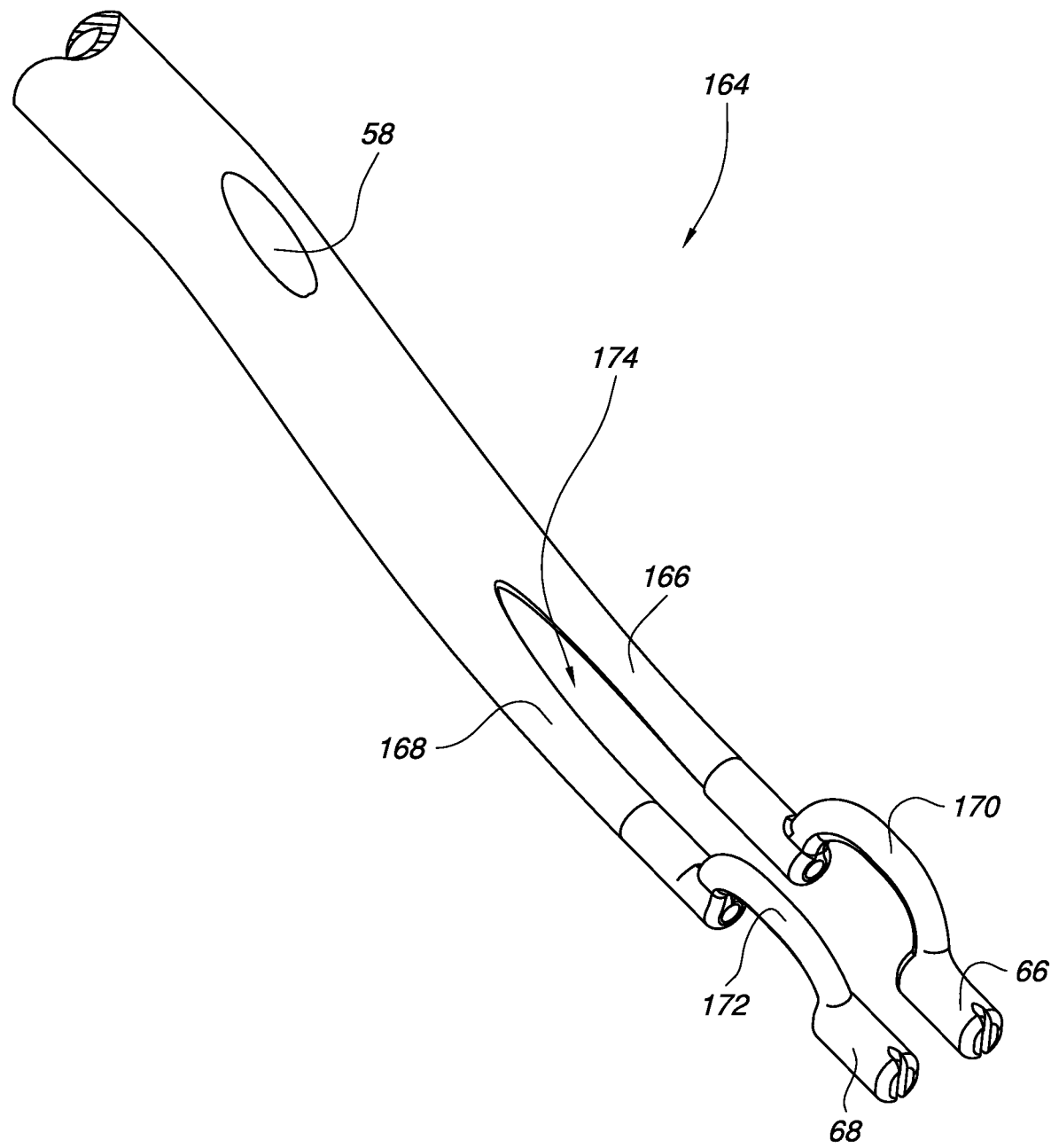
FIG. 12 illustrates a further embodiment of a forked guide tip for a surgical suturing device.

FIG. 12 illustrates a further embodiment of a forked guide tip 164 for a surgical suturing device. The embodiment of FIG. 12 is similar to previous embodiments, particularly the embodiment of FIG. 2, however it does not include any cross supports. The forked guide tip 164 has first and second legs 166, 168 which are coupled to their respective distal ends 66, 68 by respective first and second anatomical variations 170, 172. In this embodiment, a viewing area 174 is defined by the combination on one side of the first leg 166, the first anatomical variation 170, and the first distal end 66 and by the combination on the other side of the second leg 168, the second anatomical variation 172, and the second distal end 68.

Various advantages of a minimally invasive surgical suturing device for papillary muscles and methods thereof have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A surgical suturing device, comprising:
   a shaft;
   a forked guide tip comprising:
      a plurality of legs, wherein each of the plurality of legs comprises:
         a proximal end having a substantially concave shape with respect to a longitudinal axis of the shaft;
         a needle channel having a proximal channel axis substantially parallel and non-colinear to a tip axis in a first plane and substantially parallel and non-colinear to a tip axis in a second plane perpendicular to the first plane;
      a suture feed opening defined by the forked guide tip, wherein the suture feed opening is in direct communication with the shaft;
      an anatomical variation;
      a pledget holder having a pledget hole stabilizer located between the proximal end and the anatomical variation; and
      a distal end.

2. The surgical suturing device of claim 1, further comprising a shaft.

3. The surgical suturing device of claim 2, further comprising one or more needle guide tubes.

4. The surgical suturing device of claim 3, further comprising one or more supports configured to fit into the shaft and support the one or more needle guide tubes.

5. The surgical suturing device of claim 4, wherein the distal end of each of the plurality of legs defines a ferrule-receiving aperture and has a tip axis.

6. The surgical suturing device of claim 5, wherein each of the plurality of legs further comprises a needle channel in alignment with one of the one or more needle guide tubes, the needle channel having a proximal channel axis substantially parallel to the tip axis.

7. The surgical suturing device of claim 6 further comprising:
   one or more needles having a ferrule-engaging tip, each of the one or more needles movable within its own one of the one or more needle guide tubes and an aligned needle channel.

8. The surgical suturing device of claim 7, wherein at least one of the one or more supports defines a suture passage configured to receive at least a portion of a suture from the suture feed opening.

9. The surgical suturing device of claim 7, further comprising an actuator coupled to each of the one or more needles and configured to move each of the one or more needles back and forth from its needle channel towards a corresponding one of the one or more ferrule-receiving apertures.

10. The surgical suturing device of claim 2, wherein the forked guide tip is formed continuously with the shaft.

11. The surgical suturing device of claim 1, wherein each anatomical variation is sized and shaped to fit on a papillary muscle.

12. The surgical suturing device of claim 1, wherein the forked guide tip further defines a viewing area defined between the plurality of legs adjacent to the anatomical variations.

13. The surgical suturing device of claim 1, wherein the forked guide tip further comprises one or more cross supports extending between the plurality of legs.

14. The surgical suturing device of claim 13, wherein:
the one or more cross supports comprise two cross supports; and
the forked guide tip defines a viewing area between the anatomical variations and the two cross supports.

15. The surgical suturing device of claim 1, wherein the forked guide tip further defines a tissue bite area between the anatomical variations.

16. A surgical suturing device, comprising:
a shaft;
one or more needle guide tubes;
one or more supports configured to fit into the shaft and support the one or more needle guide tubes, each of the one or more supports defining a suture passage;
a forked guide tip coupled to the shaft and comprising:
a suture feed opening defined by the forked guide tip, wherein the suture feed opening is in direct communication with the shaft, in communication with the suture passage and configured to receive at least a portion of a suture;
a plurality of legs, wherein each of the plurality of legs comprises:
a proximal end having a substantially concave shape with respect to a longitudinal axis of the shaft;
an anatomical variation sized and shaped to fit on a papillary muscle;
a distal end defining a ferrule-receiving aperture and having a tip axis; and
a needle channel in alignment with one of the one or more needle guide tubes, the needle channel having a proximal channel axis substantially parallel and non-colinear to a tip axis in a first plane and substantially parallel and non-colinear to a tip axis in a second plane perpendicular to the first plane; and
one or more cross supports extending between the plurality of legs;
one or more needles having a ferrule-engaging tip, each of the one or more needles movable within its own one of the one or more needle guide tubes and the aligned needle channel;
a pledget holder having a pledget hole stabilizer located between the proximal end and the anatomical variation; and
an actuator coupled to each of the one or more needles and configured to move each of the one or more needles back and forth from its needle channel towards a corresponding one of the one or more ferrule-receiving apertures.

* * * * *